(12) United States Patent
Gruenbacher et al.

(10) Patent No.: US 8,931,711 B2
(45) Date of Patent: Jan. 13, 2015

(54) APPARATUS FOR DELIVERING A VOLATILE MATERIAL

(75) Inventors: Dana Paul Gruenbacher, Fairfield, OH (US); Jason John Olchovy, West Chester, OH (US); Scott Kendyl Stanley, West Chester, OH (US); James Douglas Still, Cleves, OH (US); Walter Sordo, Trento (IT); Stefano Deflorian, Trento (IT); Cedric Morhain, Cerdanyola del valles (ES)

(73) Assignee: The Procter & Gamble Company, Cincinnati, OH (US)

( * ) Notice: Subject to any disclaimer, the term of this patent is extended or adjusted under 35 U.S.C. 154(b) by 421 days.

(21) Appl. No.: 12/760,578

(22) Filed: Apr. 15, 2010

(65) Prior Publication Data

US 2010/0308130 A1    Dec. 9, 2010

Related U.S. Application Data

(63) Continuation-in-part of application No. 12/694,637, filed on Jan. 27, 2010, now Pat. No. 8,740,110.

(60) Provisional application No. 61/169,840, filed on Apr. 16, 2009.

(51) Int. Cl.
*A61L 9/04* (2006.01)
*A61L 9/12* (2006.01)
*A01M 1/20* (2006.01)
*A61L 9/03* (2006.01)

(52) U.S. Cl.
CPC ............... *A61L 9/12* (2013.01); *A01M 1/2033* (2013.01); *A01M 1/2044* (2013.01); *A01M 1/2072* (2013.01); *A01M 1/2077* (2013.01); *A61L 9/03* (2013.01); *A61L 9/032* (2013.01); *A61L 9/122* (2013.01)
USPC .................... 239/34; 239/57; 222/83; 222/85; 220/501

(58) Field of Classification Search
CPC .............. A61L 9/04; A61L 9/12; A61L 9/03; A61L 2209/13; A61L 9/015; A61L 2209/131; A61L 2209/133
USPC ............... 206/222, 532; 222/83, 83.5, 85, 86; 239/34–60; 220/89.3, 501, 503, 521
See application file for complete search history.

(56) References Cited

U.S. PATENT DOCUMENTS

| 3,351,495 A | 11/1967 | Larsen et al. |
| 4,161,283 A | 7/1979 | Hyman |

(Continued)

FOREIGN PATENT DOCUMENTS

| EP | 1118338 A2 | 7/2001 |
| WO | WO 9712518 A1 | 4/1997 |

(Continued)

*Primary Examiner* — Jason Boeckmann
(74) *Attorney, Agent, or Firm* — Amy I Ahn-Roll

(57) ABSTRACT

An apparatus for delivering a volatile material in a continuous manner is disclosed. The apparatus includes a delivery engine having a reservoir for containing a volatile material; a rupturable substrate secured to the reservoir; a rupture element positioned adjacent to the rupturable substrate; and a breathable membrane enclosing the reservoir, rupturable substrate and rupture element. In some embodiments, the apparatus includes a housing having a notch for compressing the rupture element and breaching the rupturable substrate as it is inserted into the housing.

14 Claims, 7 Drawing Sheets

(56) References Cited

U.S. PATENT DOCUMENTS

| | | |
|---|---|---|
| 4,339,079 A | 7/1982 | Sato et al. |
| 4,762,275 A * | 8/1988 | Herbert et al. ............... 239/6 |
| 4,824,707 A | 4/1989 | Spector |
| 5,230,867 A | 7/1993 | Kunze et al. |
| 5,455,043 A | 10/1995 | Fischel-Ghodsian |
| 5,875,968 A * | 3/1999 | Miller et al. ............... 239/44 |
| 7,481,380 B2 | 1/2009 | Kvietok et al. |
| 7,498,369 B2 | 3/2009 | Whear et al. |
| 7,754,938 B2 | 7/2010 | Rashid |
| 2003/0089791 A1* | 5/2003 | Chen et al. ............... 239/35 |
| 2005/0211790 A1 | 9/2005 | Kvietok et al. |
| 2006/0076429 A1 | 4/2006 | Kvietok et al. |
| 2006/0097065 A1 | 5/2006 | Kvietok et al. |
| 2006/0097066 A1 | 5/2006 | Kvietok et al. |
| 2006/0121269 A1* | 6/2006 | Miller et al. ............... 428/317.9 |
| 2006/0231641 A1 | 10/2006 | Uchiyama et al. |
| 2006/0233538 A1 | 10/2006 | Tollens et al. |
| 2006/0237555 A1 | 10/2006 | Cetti et al. |
| 2008/0191050 A1 | 8/2008 | Blondeau et al. |
| 2009/0188986 A1 | 7/2009 | Blondeau et al. |
| 2010/0264232 A1 | 10/2010 | Gruenbacher et al. |

FOREIGN PATENT DOCUMENTS

| | | |
|---|---|---|
| WO | WO 98/16262 A1 | 4/1998 |
| WO | WO 2006/029252 | 3/2006 |
| WO | WO 2009/024802 A1 | 2/2009 |

\* cited by examiner

APPARATUS FOR DELIVERING A VOLATILE MATERIAL

CROSS REFERENCE TO RELATED APPLICATION

This application is a continuation-in-part of U.S. application Ser. No. 12/694,637 filed Jan. 27, 2010 now U.S. Pat. No. 8,740,1110, claims priority to U.S. Provisional Application Ser. No. 61/169,840, filed Apr. 16, 2009.

FIELD OF THE INVENTION

The present invention relates to an apparatus having a breathable membrane for delivering a volatile material to the atmosphere in a continuous manner.

BACKGROUND OF THE INVENTION

It is generally known to use a device to evaporate a volatile material into a space, particularly a domestic space, in order to deliver a variety of benefits, such as air freshening or perfuming of the air. Non-energized systems, for example, systems that are not powered by electrical energy, are a popular way for the delivery of volatile materials into the atmosphere. These systems can be classified into those that require human actuation, such as aerosols, and those which do not required human actuation, such as wick based systems and gels. The first type delivers the volatile materials on demand and the second type in a more continuous manner.

One type of apparatus for delivering a volatile material is disclosed in U.S. Pat. No. 4,161,283. It discloses an article for delivering a volatile material comprising a reservoir, polymeric sheet or membrane, and a barrier layer releasably bonded to the outer wall of the reservoir. One drawback with this type of article is its susceptibility to de-lamination and leakage because the volatile materials are in contact with the membrane during storage or non-use. Another drawback may be that volatile materials build up in the membrane during storage, resulting in a spike in intensity immediately after the barrier layer is removed. Another drawback may be that the peel force makes it is difficult to remove the barrier layer without damaging the polymeric sheet or membrane. Yet another drawback may be the selectivity of the membrane in that it does not easily allow low vapor pressure volatile materials to diffuse through the polymer.

Another apparatus for delivering a volatile material is disclosed in U.S. Pat. No. 4,824,707. It discloses a decorative air freshener unit having a capsule containing a supply of volatile fragrance. The capsule is trapped between a microporous sheet and a backing sheet. The capsule is ruptured by applied force and the released fragrance is absorbed into the microporous sheet which gradually exudes the fragrance. This approach may limit the longevity of a scent since liquid is released all at once to the microporous sheet, and there is little control over the manner in which the liquid will wet the microporous sheet.

As such, there exists a need for an apparatus for delivering, over a period of time, a consistent release of volatile materials having a broad range of molecular weights and vapor pressures.

SUMMARY OF THE INVENTION

According to one embodiment of the invention, there is provided an apparatus for delivering a volatile material comprising a delivery engine having a reservoir for containing a volatile material; a rupturable substrate secured to the reservoir; a rupture element positioned adjacent to the rupturable substrate; and a microporous membrane enclosing the reservoir, rupturable substrate, and rupture element. The apparatus may deliver a volatile material in a continuous manner. In one aspect of the invention, the apparatus comprises a housing for the delivery engine. The housing may have vents for facilitating the diffusion of volatile materials from the delivery engine.

According to another embodiment of the invention, there is provided an apparatus for delivering a volatile material comprising a delivery engine having a liquid reservoir for containing a volatile material; a rupturable substrate secured to the reservoir; a compressible flange positioned adjacent to the rupturable substrate for rupturing the rupturable substrate; a collection basin in fluid communication with the liquid reservoir upon rupturing the rupturable substrate; and a breathable membrane enclosing the liquid reservoir, rupturable substrate, rupture element, and collection basin.

According to yet another embodiment of the invention, there is provided an apparatus for delivering a volatile material comprising a delivery engine having a liquid reservoir for containing a volatile material comprising a single opening; a rupturable substrate enclosing the single opening; a rupture element; a collection basin in fluid communication with the liquid reservoir upon rupturing the rupturable substrate; and a breathable membrane enclosing the liquid reservoir, rupturable substrate, rupture element, and collection basin. The breathable membrane has an evaporative surface area of about 2 $cm^2$ to about 35 $cm^2$ and has an average pore size of about 0.02 microns. The apparatus also comprises a housing for receiving and releasably engaging the delivery system. The housing has a rib for guiding the delivery engine and a notch for compressing the rupture element upon insertion of the delivery engine into the housing.

BRIEF DESCRIPTION OF THE DRAWINGS

While the specification concludes with the claims particularly pointing out and distinctly claiming the invention, it is believed that the present invention will be better understood from the following description taken in conjunction with the accompanying drawings in which:

DETAILED DESCRIPTION OF THE INVENTION

Figure 1:
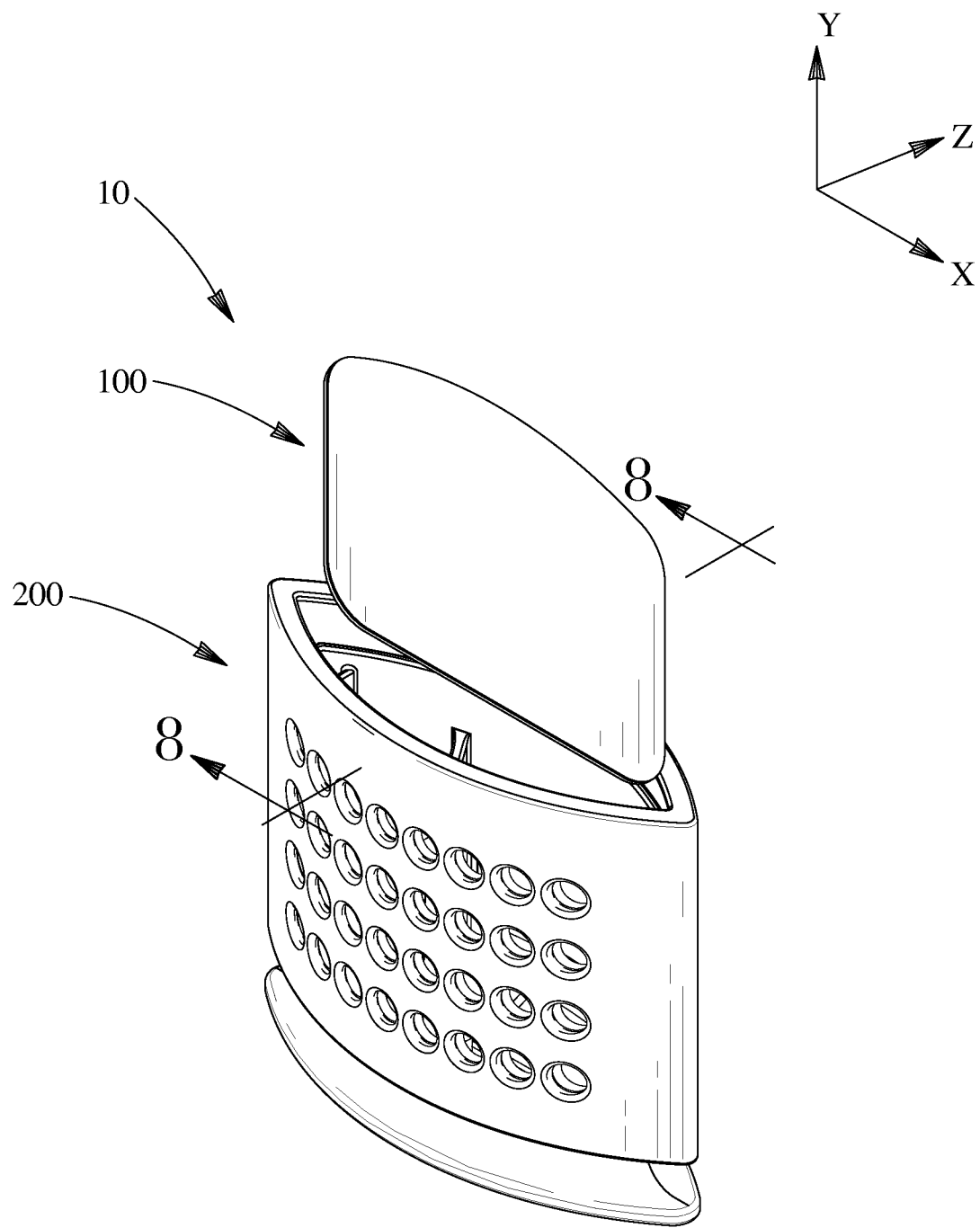
FIG. 1 shows a perspective view of one embodiment of an apparatus in accordance with the present invention.

The present invention relates to an apparatus for the delivery of a volatile material to the atmosphere. It is contemplated that the apparatus may be configured for use in a variety of applications to deliver volatile materials to the atmosphere.

For example, the apparatus may be configured for use with an energized device. An exemplary energized device may be an electrical heating device. More particularly, the device may be an electrical wall plug air freshener as described in U.S. Pat. No. 7,223,361; a battery powered heating device; or other heating devices (e.g. devices powered by chemical reactions such as catalyst fuel systems; solar powered devices, etc.). In such devices, the volatile material delivery engine may be placed next to the heating surface to diffuse the volatile material. The volatile material formula may be adjusted to include an overall lower vapor pressure formula.

The apparatus may also be configured for use with an air purifying system to deliver both purified air and volatile materials to the atmosphere. Non-limiting examples include air purifying systems using ionization and/or filtration technology for use in small spaces (e.g. bedrooms, bathrooms, automobiles, etc.), and whole house central air conditioning/heating systems (e.g. HVAC).

The apparatus may also be configured for use with an aerosol or non-aerosol air spray. In this embodiment, the delivery engine can deliver volatile materials upon user demand or programmed to automatically deliver volatile materials to the atmosphere.

The apparatus may also be configured for use with a fan to deliver volatile materials to the atmosphere.

For purposes of illustrating the present invention in detail, the invention is described below in a non-energized system. "Non-energized" means that the apparatus is passive does not require to be powered by a source of external energy. In particular, the apparatus does not need to be powered by a source of heat, gas, or electrical current, and the volatile material is not delivered by aerosol means.

In the non-energized embodiment, the apparatus of the present invention delivers a volatile material in a substantially continuous manner when the apparatus is in a resting position (i.e. the apparatus is not being moved). The emission level of volatile materials may exhibit a uniform intensity until substantially all the volatile materials are exhausted. The continuous emission of the volatile materials can be of any suitable length, including but not limited to, up to: 20 days, 30 days, 60 days, 90 days, shorter or longer periods, or any period between 30 to 90 days.

The apparatus of the present invention is suitable for purposes of providing fragrances, air fresheners, deodorizers, odor eliminators, malodor counteractants, insecticides, insect repellants, medicinal substances, disinfectants, sanitizers, mood enhancers, and aromatherapy aids, or for any other purpose using a volatile material that acts to condition, modify, or otherwise change the atmosphere or the environment. For purposes of illustrating the present invention in detail, but without intending to limit the scope of the invention, the invention will be described in an air freshening system for delivering liquid containing perfume raw materials.

Referring to FIG. 1, an apparatus 10 in accordance with the present invention is shown. The apparatus 10 includes a delivery engine 100 and a housing 200.

Delivery Engine

Figure 2:
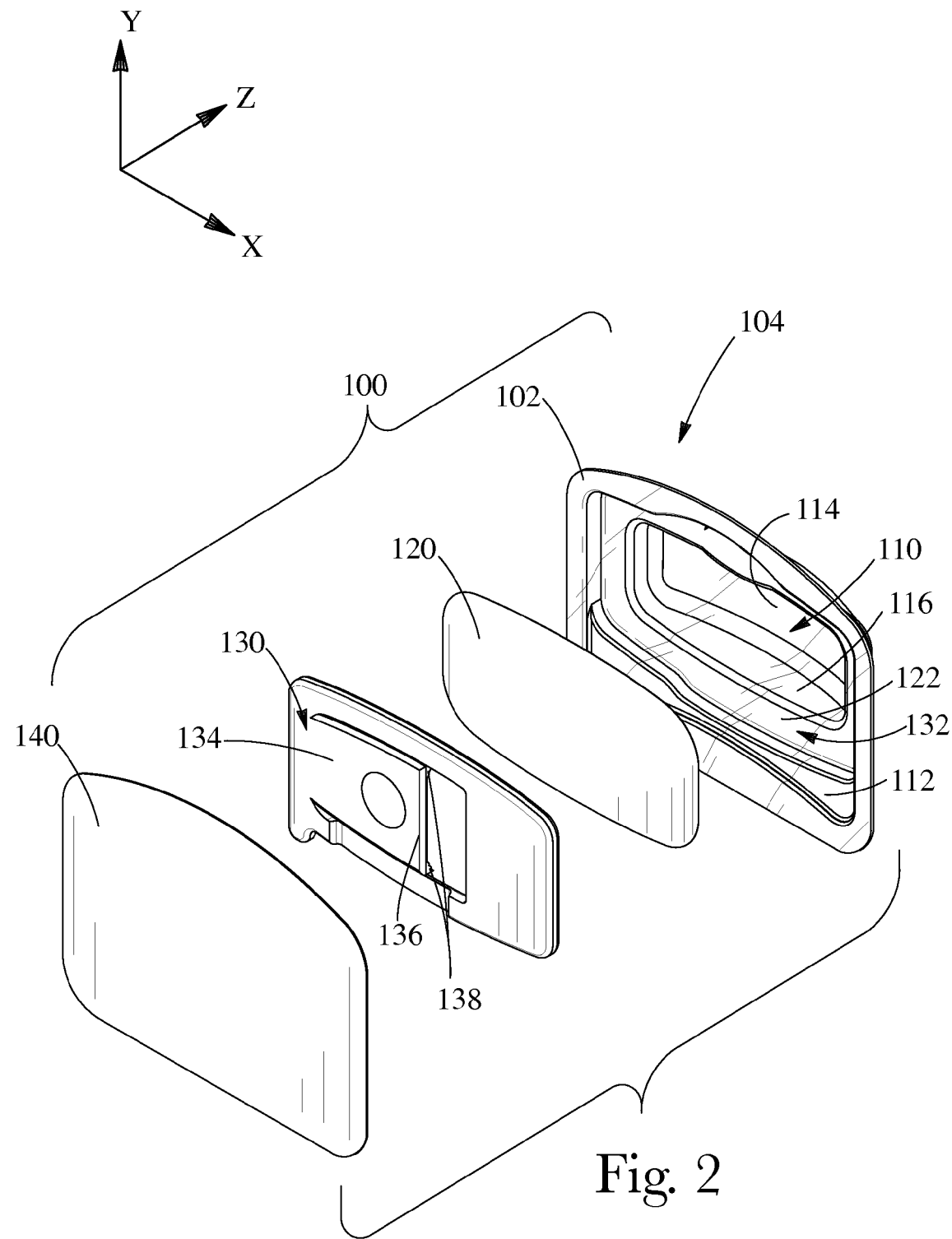
FIG. 2 shows an exploded, perspective view of one embodiment of a delivery engine in accordance with the present invention.

Referring to FIG. 2, the delivery engine 100 comprises a width, length and depth along an x-axis, y-axis, and z-axis, respectively. The width, length, and depth may be such that the delivery engine 100 is considered compact and/or portable. By "compact" or "portable", it is meant that the delivery engine 100 can be conveniently and comfortably carried in a pocket, purse, or the like. The delivery engine 100 can be constructed as a disposable, single-use item or one that it is replenished with a volatile material.

The delivery engine 100 may include a lip 102 that defines the outer perimeter of the delivery engine 100 and may circumference a reservoir 110 for containing a volatile material as well as a collection basin 112. The delivery engine 100 may also include a rupturable substrate 120 secured to the reservoir 110; a rupture element 130 positioned adjacent to the rupturable substrate 120; and a breathable membrane 140 secured to the lip 102 and enclosing the rupturable substrate 120, reservoir 110, and collection basin 112.

The body 104 of the delivery engine 100 can be thermoformed, injection molded, or blow molded with any known material. In some embodiments, the body 104 includes all structural aspects of the delivery engine 100 minus the rupturable substrate 120, the rupture element 130, and breathable membrane 140. In other embodiments, the body 104 includes the rupture element 130. The body 104 may be made of a multi layer material which may include a barrier layer to prevent evaporation of a volatile component and at least one outer layer that allows a rupturable substrate 120 to be heat-sealed to the body 104. A suitable sealant layer would include a layer of polyethylene or polypropylene or any suitable polyolefin sealant that allows for a leak proof seal of the reservoir 110. Suitable materials to form the body 104 of the delivery engine 100 include plastics, such as Pentaplast Pentaform® 2101 available from Klockner. In some embodiments, the material is colored or non-colored see-through plastic. The see-through material permits observation of the liquid and end-of life.

Reservoir

The delivery engine 100 may comprise a reservoir 110 for holding a volatile material. The reservoir 110 includes a width, length, and depth along the x-axis, y-axis, and z-axis, respectively. The reservoir 110 may be elongate in that its width to length ratio is about 2:1 to about 4:1, alternatively about 1.5:1 to about 2.5:1. The reservoir 110 may have a width of about 45 mm to about 55 mm, alternatively about 51 mm; a length of about 15 mm to about 30 mm to about, alternatively about 23 mm; a depth of about 5 mm to about 15 mm, alternatively about 11 mm. The dimensions of the reservoir 110 may be such that it holds about 2 ml to about 50 ml of liquid containing a volatile material. Alternatively, the reservoir 110 may hold about 2 ml to about 30 ml, alternatively about 2 ml to about 10 ml, alternatively about 2 ml to about 8 ml, alternatively about 4 ml to about 6 ml, alternatively about 2 ml, alternatively about 6 ml of liquid containing a volatile material.

The reservoir 110 may include a bottom 114 and a single opening 116. The reservoir 110 may also have a ridge 122 circumferencing the single opening 116 or the upper edge of the reservoir 110. This ridge 122 may provide a generally flat surface upon which a rupturable substrate 120 may be secured. The ridge 122 allows the secured area of the rupturable substrate 120 to be located away from the inner walls of the reservoir 110 where the volatile material would be held.

It is contemplated that the delivery engine 100 of the present invention may comprise two or more reservoirs (not shown) which can be filled with the same or different volatile materials. The reservoirs may have any configuration that contacts the breathable membrane 140 upon rupture. For example, the reservoirs may be opposely connected for use in a flippable device. In such a device, the breathable membrane 140 is fluidly connected between the reservoirs.

Rupturable Substrate

Still referring to FIG. 2, the delivery engine 100 includes a rupturable substrate 120. The rupturable substrate 120 may be configured in any manner that prevents the volatile material in the reservoir 110 from contacting the breathable membrane 140 prior to activating or rupturing the delivery engine 100. In one embodiment, the rupturable substrate 120 may enclose the reservoir, prior to activation, by extending across the single opening 116 securing to the ridge 122 of the reservoir 110. The rupturable substrate 120 may be secured by a layer of adhesives, heat and/or pressure sealing, ultrasonic bonding, crimping, and the like or a combination thereof.

The rupturable substrate 120 can be made of any material that ruptures with applied force, with or without the presence of an element to aid in such rupture. Because the rupturable substrate 120 is intended to contain a volatile material while in storage, it may be made from a layer of barrier material that prevents evaporation of the volatile material prior to its intended use and a layer of heat-sealable layer. Such materials may be impermeable to vapors and liquids. Suitable barrier materials for the rupturable substrate 120 include a flexible film, such as a polymeric film, a flexible foil, or a composite material such as foil/polymeric film laminate. Suitable flexible foils include a metal foil such as a foil comprised of a nitrocellulose protective lacquer, a 20 micron aluminum foil, a polyurethane primer, and 15 g/m2 polyethylene coating (Lidfoil 118-0092), available from Alcan Packaging. Suitable polymeric films include polyethylene terephtalate (PET) films, acrylonitrile copolymer barrier films such as those sold under the tradename Barex® by INOES, ethylene vinyl alcohol, and combinations thereof. It is also contemplated that coated barrier films may be utilized as a rupturable substrate 120. Such coated barrier films include metalized PET, metalized polypropylene, silica or alumina coated film may be used. Any barrier material, whether coated or uncoated, may be used alone and or in combination with other barrier materials.

Rupture Element

The rupturable substrate 120 may be breached to release a volatile material by actuating a rupture element 130. The rupture element 130 can be injection, compression, or pressure molded using a polyolefin, such as polyethylene or polypropylene; polyester; or other plastics as known to be suitable for molding. The rupture element 130 could also be made by thermoforming with a discrete cutting step to remove parts not wanted.

The rupture element 130 may be positioned in a space 132 formed in the delivery engine body 104 that is adjacent to the rupturable substrate 120 and subjacent a breathable membrane 140. The space 132 may be configured such that the rupture element 132 is nested within the space 132 and enclosed by a breathable membrane 140, thus requiring no other means to hold the rupture element 132 in the delivery engine 100. In one embodiment, the rupture element 130 is positioned between and in contact with said rupturable substrate 120 and said breathable membrane 140. A rupture element 130 that is directly adjacent to the breathable membrane 140 may facilitate wetting of the breathable membrane 140. More specifically, liquid may wick between rupture element 130 and the breathable membrane 140 allowing for maintenance of a larger wetted surface area of the breathable membrane 140.

The rupture element 130 may be configured in any manner such that a user can manually actuate the rupture element 130 and breach the rupturable substrate 120 with relative ease. In one embodiment, a user may actuate the rupture element 130 by manually compressing it. In other embodiments, the rupture element 130 may breach the rupturable substrate 120 through contact with an element provided in a delivery engine housing that engages and compresses the rupture element 130. Suitable compression forces to breach the rupturable substrate 120 with a rupture element 130 may be less than about 25N, alternatively, less than about 20N, alternatively less than about 15N, alternatively less than about 10N, alternatively less than about 5N, alternatively from about 1N to about 15N, alternatively, from about 1N, to about 10N, alternatively, from about 1N to about 5N.

The compression force can be measured using an electromechanical testing system, QTest Elite 10, available from MTS, along with a modified UL 283 finger probe made of polyamide. The UL 283 finger probe is described in *Standard for Air Fresheners and Deodorizers*, UL Standard 283, FIG. 10.1 (UL Mar. 31, 2004). As described in UL 283, FIG. 10.1, the radius of the finger tip is 3.5 mm; height of the finger tip is 5 mm; depth of the finger tip is 5.8 mm. However, unlike the finger probe described in the aforementioned text, the modified UL 283 finger probe does not include any articulating joints. Instead, it is in a fixed position that is perpendicular to the rupture element 130 when testing is conducted. The testing occurs at ambient temperatures (23±2° C.). The perimeter of a delivery engine 100 is rested on a support fixture, without directly contacting or directly securing the rupture element 130 to the support fixture. The crosshead speed of the electromechanical testing system is set at 30 mm/min. The modified UL 283 finger probe is moved towards the rupture element 130 to contact a region where displacement is desired for rupturing a rupturable substrate 120. Where a flange 134 such as the one described herein is utilized, the desired region of displacement is the mid-point of the flange 134. The mid-point is the point that is half way between the proximal end and distal end 136. For example, where a flange 134 is 2 cm from proximal end to distal end 136, the mid-point is located at 1 cm. The machine is run until the rupture element 130 is displaced by 6 mm. Zero displacement is defined as the point at which 0.1N of force (i.e. preload) is applied. The load at the first peak where the rupturable substrate 120 is broken is recorded as the force to rupture. Those of ordinary skill in the art will appreciate that compression forces will vary depending on the physical properties and placement of the breathable membrane 140, rupture element 130, and rupturable substrate 120 in a delivery engine 100.

There are numerous embodiments of the rupture element 130 described herein, all of which are intended to be non-limiting examples. FIG. 2 shows one non-limiting embodiment of the rupture element 130. In this embodiment, the rupture element 130 includes a flange 134 hinged to the rupture element 130. The flange 134 may be injection molded and may include a distal end 136. The distal end 136 may include one or more piercing elements 138 located in the z-direction or towards the rupturable substrate 120. In one embodiment, the distal end 136 may include two spaced apart piercing elements 138 in the z-direction. In an alternate embodiment, the distal end 136 may form a single point (not shown) along the x-y plane. A user may manually compress or press downward in the z-direction on the flange 134 such that the rupturable substrate 120 is breached and a volatile material is released to the breathable membrane 140.

It is contemplated that the rupture element 130 may include more than one flange 134 where additional points of rupture are desired. For example, the rupture element 130 may include a first compressible flange and a second compressible flange opposedly hinged to said rupture element (not shown).

Figure 3:
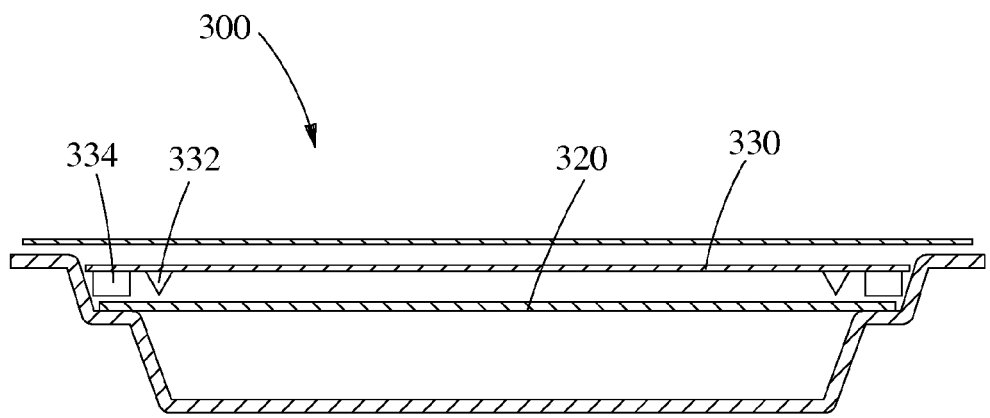
FIG. 3 shows a cross-sectional view of another embodiment of a rupture element in accordance with the present invention.

FIG. 3 shows another embodiment of a rupture element 330 which includes one or more piercing elements 332 supported on a corresponding spring-like part 334. The spring-like part 334 may be a metal coil, polyolefin or polyurethane foam, injection molded bristles, injection molded plastic spring or hinge parts, or the like. Upon pressing the rupture element 330 towards the rupturable substrate 320, one or more piercing elements 332 will puncture the rupturable substrate 320 and then return to its original position.

Figure 4:
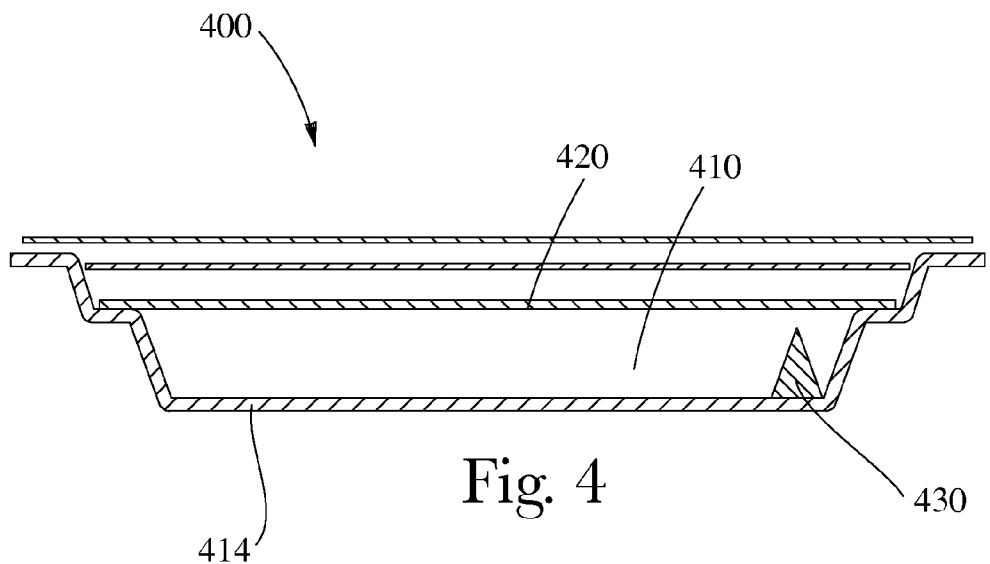
FIG. 4 shows a cross-sectional view of another embodiment of a rupture element in accordance with the present invention.

FIG. 4 shows another embodiment of a rupture element 430 where it is integrally formed with the reservoir 410. This can be accomplished by thermoforming, pressure forming, injection molding or any known means of forming plastic parts. The rupture element 430 in this embodiment, is a sharp piercing structure extending opposite from the interior bottom 414 of the reservoir. A user may compress the bottom 414 of the reservoir 410 to pierce the rupturable substrate 420 with the rupture element 430. This embodiment eliminates having to manufacture a separate rupture element 430, yet it performs the same function.

Collection Basin

Figure 5:
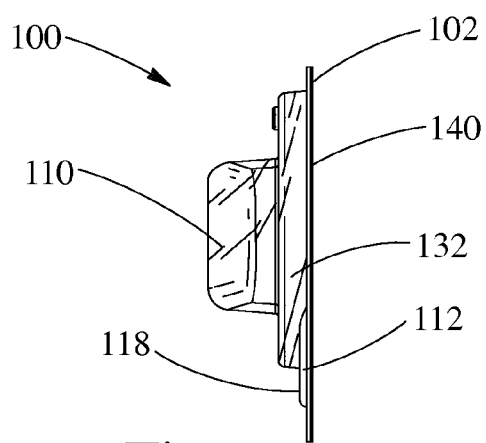
FIG. 5 shows a side elevational view of the delivery engine in FIG. 2 in accordance with the present invention.
Figure 6:
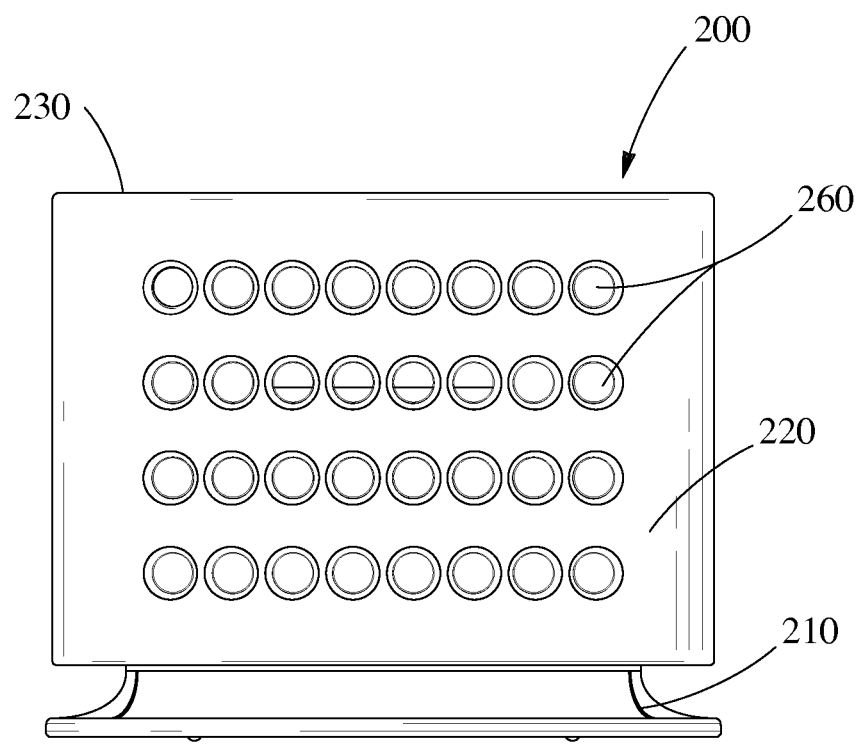
FIG. 6 shows a front elevational view of one embodiment of a housing in accordance with the present invention.
Figure 7:
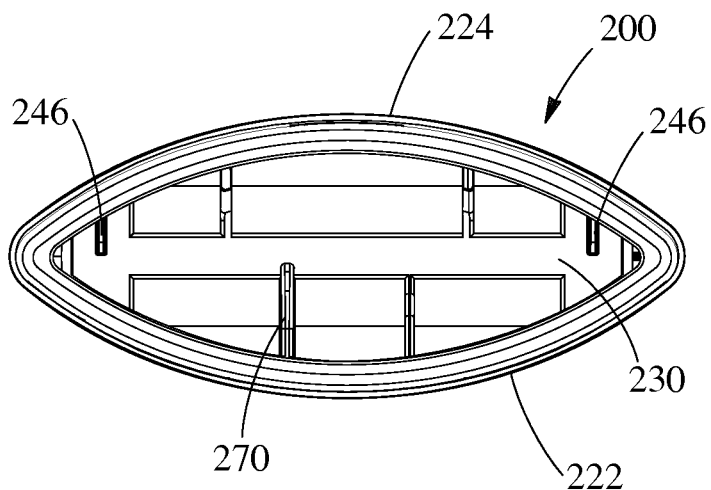
FIG. 7 shows a top plan view of the housing in FIG. 6.

Now referring to FIG. 5, the delivery engine 100 may optionally include a collection basin 112 to collect volatile materials from the reservoir 110 after the rupturable substrate 120 is compromised. The collection basin 112 may be any size, shape or configuration, and may be made of any suitable material, so long as it is in fluid communication with the reservoir 110 and the breathable membrane 140 upon rupturing the rupturable substrate 120. It may be sized to collect any suitable volume of a volatile material to provide a controlled volume of the volatile material to the breathable membrane 140. In one embodiment, the collection basin 112 may be sized to collect about 1 ml to about 4 ml of volatile materials, alternatively about 1 ml to about 3 ml, alternatively about 1 ml to about 2.5 ml, alternatively about 1.5 ml to about 1.8 ml.

In one embodiment, the collection basin 112 may include a bottom 118 in the z-direction and a top that opens towards a breathable membrane 140. The breathable membrane 140 may lie across the open top, enclosing the collection basin 112 so liquid cannot flow freely out through the breathable membrane 140. The collection basin 112 may be integrally constructed with the body 104 of the delivery engine 100 in a thermoform part.

As shown in FIG. 5, in one embodiment, the collection basin 112 is positioned downwardly or opposite the y-direction from the reservoir 110. When the delivery engine 100 is placed upright, a volatile material naturally flows down the reservoir 110 into the collection basin 112 ensuring a controlled, continual dosing of the breathable membrane 140. Further, the collection basin 112 has depth along the z-axis which is smaller in depth than the reservoir 110. The bottom 118 of the collection basin lies closer to the breathable membrane 140 than the reservoir bottom 114, thus forming a step in the delivery engine 100. The proximity of the collection basin bottom 118 with the breathable membrane 140 helps to ensure a continual supply of volatile material and wet more surface area of the breathable membrane 140, even when very little volatile material remains in the delivery engine 100. When the liquid contact area of the breathable membrane 140 is greater, the evaporation rate of volatile materials is higher and fragrance intensity can be maintained over longer periods.

Membrane

The delivery engine 100 may include a breathable membrane 140. The breathable membrane 140 is vapor permeable and prevents free flow of liquid out of the membrane 140, thus addressing leakage problems.

The breathable membrane 140 may be secured to the lip 102 of the delivery engine 100 in the same manner as the rupturable substrate 120 is secured to the ridge 122 of the reservoir 110. The breathable membrane 140 encloses the reservoir 110, rupturable substrate 120, rupture element 130, and collection basin 112. In this way, the rupturable substrate 120 may be breached by compressing the breathable membrane 140 and the rupture element 130. Once breached, the volatile material flows out of the reservoir 110, contacts the breathable membrane 140, and is delivered to the atmosphere. Because the breathable membrane 140 is shielded from the volatile material until the rupturable substrate 120 is breached, the fragrance intensity may build slowly from zero to its equilibrium rate of release when the breathable membrane 140 is fully wetted.

While not wishing to be bound by theory, the physical characteristics of a membrane may affect the diffusion or transfer rate of volatile materials through the membrane. Such characteristics may include materials used, use of fillers, pore size, thickness, and evaporative surface area.

As used herein, the "volatile material contact surface" is that surface of the microporous membrane that faces and typically is in contact with the volatile material, which is, for example, contained in a test reservoir, as described in further detail below.

As used herein, the "vapor release surface" is that surface of the microporous membrane that does not face and/or contact directly the volatile material, and from which volatile material is released into an exterior atmosphere in a gaseous or vapor form.

As used herein, the term "(meth)acrylate" and similar terms, such as "esters of (meth)acrylic acid" means acrylates and/or methacrylates.

As used herein, the "volatile material transfer rate" of the microporous membrane, was determined in accordance with the following description. A test reservoir was fabricated from a clear thermoplastic polymer, having interior volume sufficient to contain 2 milliliters of volatile material such as benzyl acetate. The interior dimensions of the reservoir was defined by a circular diameter at the edge of the open face of approximately 4 centimeters and a depth of no greater than 1 centimeter. The open face was used to determine the volatile material transfer rate. With the test reservoir laying flat (with the open face facing upward), about 2 milliliters of benzyl acetate was introduced into the test reservoir. With benzyl acetate introduced into the test reservoir, a sheet of microporous membrane having a thickness of from 6 to 18 mils was placed over the open face/side of the test reservoir, such that 10 cm$^2$ of the volatile material contact surface of the microporous membrane was exposed to the interior of the reservoir. The test reservoir was weighed to obtain an initial weight of the entire charged assembly. The test reservoir, containing benzyl acetate and enclosed with the sheet of microporous membrane, was then placed, standing upright, in a laboratory chemical fume hood having approximate dimensions of 5 feet (height)×5 feet (width)×2 feet (depth). With the test reservoir standing upright, benzyl acetate was in direct contact with at least a portion of the volatile material contact surface of the microporous membrane. The glass doors of the fume hood were pulled down, and the air flow through the hood was adjusted so as to have 8 turns (or turnovers) of hood volume per hour. Unless otherwise indicated, the temperature in the hood was maintained at 25° C.±5° C. The humidity within in the fume hood was ambient. The test reservoirs were regularly weighed in the hood. The calculated weight loss of benzyl acetate, in combination with the elapsed time and surface area of the microporous membrane exposed to the interior of the test reservoir, were used to determine the volatile transfer rate of the microporous membrane, in units of mg/(hour, cm$^2$).

As used herein, the percent increase in volatile material transfer rate of the microporous membrane of the present invention from 25° C. to 60° C. was determined for separate but substantially equivalent microporous membrane samples at 25° C. and 60° C., in accordance with the method described above. Reservoirs were placed in a large glass bell jar and over a 50% aqueous solution of potassium chloride also contained in the bell jar. The entire bell jar with contents was placed in an oven heated to 60° C. The reservoirs were held under these conditions for a period of 7 to 10 hours. The reservoirs were then returned to the hood at ambient conditions overnight and the process was repeated over several days. Each of the reservoirs was weighed before being placed in the bell jar and after being removed from the bell jar. Upon removal from the bell jar, the weight of each reservoir was taken after the reservoir had returned to ambient temperature.

As used herein, whether the vapor release surface of the microporous membrane is "substantially free of volatile material in liquid form" was determined in accordance with the following description. When the test reservoirs were weighed, as described above, the vapor release surface of the microporous membrane was examined visually by naked eye to determine if drops and/or a film of liquid were present there-on. If any evidence of drops (i.e., a single drop) and/or a film of liquid was visually observed on the vapor release surface, but did not run off the surface, the microporous membrane was considered to be acceptable. If the drops ran off the surface, the microporous membrane was determined to have failed. If no evidence of drops (i.e., not one drop) and/or a film of liquid was visually observed on the vapor release surface, the microporous membrane was determined to be substantially free of volatile material in liquid form.

Transfer Rate

The volatile material transfer rate of the microporous membrane can be less than or equal to 0.7 mg/(hour*cm$^2$), or less than or equal to 0.6 mg/(hour*cm$^2$), or less than or equal to 0.55 mg/(hour*cm$^2$), or less than or equal to 0.50 mg/(hour*cm$^2$). The volatile material transfer rate of the microporous membrane can be equal to or greater than 0.02 mg/(hour*cm$^2$), or equal to or greater than 0.04 mg/(hour*cm$^2$), or equal to or greater than 0.30 mg/(hour*cm$^2$), or equal to or greater than 0.35 mg/(hour*cm$^2$). The volatile material transfer rate of the microporous membrane may range between any combination of these upper and lower values. For example, the volatile material transfer rate of the microporous membrane can be from 0.04 to 0.6 mg/(hour*cm$^2$), or from 0.2 to 0.6 mg/(hour*cm$^2$), or from 0.30 to 0.55 mg/(hour*cm$^2$), or from 0.35 to 0.50 mg/(hour*cm$^2$), in each case inclusive of the recited values.

While not intending to be bound by any theory, when volatile material is transferred from the volatile material contact surface to the vapor release surface of the microporous membrane, it is believed that the volatile material is in a form selected from liquid, vapor, and a combination thereof. In addition, and without intending to be bound by any theory, it is believed that the volatile material, at least in part, moves through the network of interconnecting pores that communicate substantially throughout the microporous membrane.

Density and Coatings

The microporous membrane can have a density of at least 0.7 g/cm$^3$, such as at least 0.8 g/cm$^3$. As used herein, the density of the microporous membrane is determined by measuring the weight and volume of a sample of the microporous membrane. The upper limit of the density of the microporous membrane may range widely, provided it has a targeted volatile material transfer rate of, for example, from 0.04 to 0.6 mg/(hour*cm$^2$), and the vapor release surface is substantially free of volatile material in liquid form when volatile material is transferred from the volatile material contact surface to said vapor release surface. Typically, the density of the microporous membrane is less than or equal to 1.5 g/cm$^3$, or less than or equal to 1.2 g/cm$^3$, or less than or equal to 1.0 g/cm$^3$. The microporous membrane can have a density of from 0.7 g/cm$^3$ to 1.5 g/cm$^3$, for example, from 0.8 g/cm$^3$ to 1.2 g/cm$^3$, inclusive of the recited values.

When the microporous membrane has a density of at least 0.7 g/cm$^3$, such as at least 0.8 g/cm$^3$, the volatile material contact surface and the vapor release surface of the microporous membrane each may be free of a coating material thereon. When free of a coating material thereon, the volatile material contact surface and the vapor release surface each are defined by the microporous membrane.

When the microporous membrane has a density of at least 0.7 g/cm$^3$, such as at least 0.8 g/cm$^3$, at least a portion of the volatile material contact surface of the microporous membrane, optionally, may have a first coating thereon, and/or at least a portion of the vapor release surface of the microporous membrane, optionally, may have a second coating thereon. The first coating and the second coating may be the same or different. When at least a portion of the volatile material contact surface has a first coating thereon, the volatile material contact surface is defined at least in part by the first coating. When at least a portion of the vapor release surface has a second coating thereon, the vapor release surface is defined at least in part by the second coating.

The first coating and the second coating may each be selected from liquid coatings and solid particulate coatings (e.g., powder coatings). Typically, each of the first and second coatings independently is selected from liquid coatings which may optionally include a solvent selected from water, organic solvents and combinations thereof. The first and second coatings each independently may be selected from crosslinkable coatings (e.g., thermosetting coatings and photo-curable coatings), and non-crosslinkable coatings (e.g., air-dry coatings). The first and second coatings may be applied to the respective surfaces of the microporous membrane in accordance with art-recognized methods, such as spray application, curtain coating, dip coating, and/or drawn-down coating (e.g., by means of a doctor blade or draw-down bar) techniques.

The first and second coating compositions each independently can include art-recognized additives, such as antioxidants, ultraviolet light stabilizers, flow control agents, dispersion stabilizers (e.g., in the case of aqueous dispersions), and colorants (e.g., dyes and/or pigments). Typically, the first and second coating compositions are free of colorants, and are as such substantially clear or opaque. Optional additives may be present in the coating compositions in individual amounts of from, for example, 0.01 to 10 percent by weight, based on the total weight of the coating composition.

The first coating and said second coating each independently can be formed from an aqueous coating composition that includes dispersed organic polymeric material. The aqueous coating composition may have a particle size of from 200 to 400 nm. The solids of the aqueous coating composition may vary widely, for example from 0.1 to 30 percent by weight, or from 1 to 20 percent by weight, in each case based on total weight of the aqueous coating composition. The organic polymers of the aqueous coating compositions may have number average molecular weights (Mn) of, for example, from 1000 to 4,000,000, or from 10,000 to 2,000,000.

The aqueous coating composition can be selected from aqueous poly(meth)acrylate dispersions, aqueous polyurethane dispersions, aqueous silicone (or silicon) oil dispersions, and combinations thereof. The poly(meth)acrylate polymers of the aqueous poly(meth)acrylate dispersions may be prepared in accordance with art-recognized methods. For example, the poly(meth)acrylate polymers may include residues (or monomer units) of alkyl (meth)acrylates having from 1 to 20 carbon atoms in the alkyl group. Examples of alkyl (meth)acrylates having from 1 to 20 carbon atoms in the alkyl group include, but are not limited to, methyl (meth)acrylate, ethyl (meth)acrylate, 2-hydroxyethyl (meth)acrylate, propyl (meth)acrylate, 2-hydroxypropyl (meth)acrylate, isopropyl (meth)acrylate, butyl (meth)acrylate, isobutyl (meth)acrylate, tert-butyl (meth)acrylate, 2-ethylhexyl (meth)acrylate, lauryl (meth)acrylate, isobornyl (meth)acrylate, cyclohexyl (meth)acrylate, and 3,3,5-trimethylcyclohexyl (meth)acrylate. For purposes of non-limiting illustration, an example of an aqueous poly(meth)acrylate dispersion from which the first and second coating compositions may each be independently selected is HYCAR 26138, which is commercially available from Lubrizol Advanced Materials, Inc.

The polyurethane polymers of the aqueous polyurethane dispersions, from which the first and second coatings each independently may be selected, include any of those known to the skilled artisan. Typically the polyurethane polymers are prepared from isocyanate functional materials having two or more isocyanate groups, and active hydrogen functional materials having two or more active hydrogen groups. The active hydrogen groups may be selected from, for example, hydroxyl groups, thiol groups, primary amines, secondary amines, and combinations thereof. For purposes of non-limiting illustration, an example of an aqueous polyurethane dispersion from which the first and second coating compositions may each be independently selected is WITCOBOND W-240, which is commercially available from Chemtura Corporation.

The silicon polymers of the aqueous silicone oil dispersions may be selected from known and art-recognized aqueous silicone oil dispersions. For purposes of non-limiting illustration, an example of an aqueous silicon dispersion from which the first and second coating compositions may each be independently selected is MOMENTIVE LE-410, which is commercially available from Momentive Performance Materials.

The first coating and the second coating each independently can be applied at any suitable thickness, provided the microporous membrane has a targeted volatile material transfer rate of, for example, from 0.04 to 0.6 mg/(hour*cm$^2$), and the vapor release surface is substantially free of volatile material in liquid form when volatile material is transferred from the volatile material contact surface to said vapor release surface. Also, the first coating and the second coating each independently can have a coating weight (i.e., the coating on the microporous membrane) of from 0.01 to 5.5 g/m$^2$, such as from 0.1 to 5.0 g/m$^2$, or from 0.5 to 3 g/m$^2$, or from 0.75 to 2.5 g/m$^2$, or from 1 to 2 g/m$^2$.

The microporous membrane can have a density of less than 0.8 g/cm$^3$, and at least a portion of the volatile material contact surface of the microporous membrane can have a first coating thereon, and/or at least a portion of the vapor release surface of the microporous membrane can have a second coating thereon. The first coating and the second coating may be the same or different, and each independently is as described previously herein with regard to the optional first and second coatings of the microporous membrane having a density of at least 0.7 g/cm$^3$.

When less than 0.7 g/cm$^3$, the density of the microporous membrane of the present invention may have any suitable lower limit, provided the microporous membrane has a targeted volatile material transfer rate of, for example, from 0.04 to 0.6 mg/(hour*cm$^2$), and the vapor release surface is substantially free of volatile material in liquid form when volatile material is transferred from the volatile material contact surface to said vapor release surface. With this particular embodiment of the present invention, the density of the microporous membrane may be from 0.6 to less than 0.8 g/cm$^3$, or from 0.6 to 0.75 g/cm$^3$ (e.g., from 0.60 to 0.75 g/cm$^3$) or from 0.6 to 0.7 g/cm$^3$ (e.g., from 0.60 to 0.70 g/cm$^3$), or from 0.65 to 0.70 g/cm$^3$.

Further, at least a portion of the volatile material contact surface of the microporous membrane can have a first coating thereon, and/or at least a portion of the vapor release surface of the microporous membrane can have a second coating thereon, in which each of the first and second coatings independently is selected from a coating composition comprising a poly(vinyl alcohol).

With the poly(vinyl alcohol) coated embodiment of the present invention, when the microporous membrane (i.e., the poly(vinyl alcohol) coated microporous membrane) is exposed to a temperature increase of from 25° C. to 60° C., the volatile material transfer rate thereof increases by less than or equal 150 percent. When the poly(vinyl alcohol) coated microporous membrane) is exposed to a temperature increase (e.g., from an ambient temperature of from 25° C. to 60° C.) the volatile material transfer rate typically increases, and typically does not decrease unless, for example, the microporous membrane has been damaged by exposure to the higher ambient temperature. As such, and as used herein and in the claims, the statement "the volatile material transfer rate thereof increases by less than or equal to [a stated] percent" (e.g., 150 percent), is inclusive of a lower limit of 0 percent, but is not inclusive of a lower limit that is less than 0 percent.

For purposes of illustration, when the poly(vinyl alcohol) coated microporous membrane has a volatile material transfer rate of 0.3 mg/(hour*cm$^2$) at 25° C., when the microporous membrane is exposed to a temperature of 60° C., the volatile material transfer rate increases to a value that is less than or equal to 0.75 mg/(hour*cm$^2$).

In an embodiment of the present invention, when the microporous membrane (i.e., the poly(vinyl alcohol) coated microporous membrane) is exposed to a temperature increase of from 25° C. to 60° C., the volatile material transfer rate thereof increases by less than or equal 125 percent. For example, when the poly(vinyl alcohol) coated microporous membrane has a volatile material transfer rate of 0.3 mg/(hour*cm$^2$) at 25° C., when the microporous membrane is exposed to a temperature of 60° C., the volatile material transfer rate increases to a value that is less than or equal to 0.68 mg/(hour*cm$^2$).

Further, when the microporous membrane (i.e., the poly(vinyl alcohol) coated microporous membrane) is exposed to a temperature increase of from 25° C. to 60° C., the volatile material transfer rate thereof increases by less than or equal 100 percent. For example, when the poly(vinyl alcohol) coated microporous membrane has a volatile material transfer rate of 0.3 mg/(hour*cm$^2$) at 25° C., when the microporous membrane is exposed to a temperature of 60° C., the volatile material transfer rate increases to a value that is less than or equal to 0.6 mg/(hour*cm$^2$).

The first and second poly(vinyl alcohol) coatings each independently may be present in any suitable coating weight, provided the microporous membrane has a targeted volatile material transfer rate of, for example, at least 0.04 mg/(hour*cm$^2$), and when the microporous membrane (i.e., the poly(vinyl alcohol) coated microporous membrane) is exposed to a temperature increase of from 25° C. to 60° C., the volatile material transfer rate thereof increases by less than or equal to 150 percent. Typically, the first poly(vinyl alcohol) coating and the second poly(vinyl alcohol) coating each independently have a coating weight of from 0.01 to 5.5 g/m$^2$, such as from 0.1 to 4.0 g/m$^2$, or from 0.5 to 3.0 g/m$^2$, or from 0.75 to 2.0 g/m$^2$.

The volatile material transfer rate of the poly(vinyl alcohol) coated microporous membrane can be at least 0.02 mg/(hour*cm$^2$). The volatile material transfer rate of the poly(vinyl alcohol) coated microporous membrane may be equal to or greater than 0.04 mg/(hour*cm$^2$), or equal to or greater than 0.1 mg/(hour*cm$^2$), or equal to or greater than 0.2 mg/(hour*cm$^2$), equal to or greater than 0.30 mg/(hour*cm$^2$), or equal to or greater than 0.35 mg/(hour*cm$^2$). The volatile material transfer rate of the poly(vinyl alcohol) coated microporous membrane may be less than or equal to 0.7 mg/(hour*cm$^2$), or less than or equal to 0.6 mg/(hour*cm$^2$), or less than or equal to 0.55 mg/(hour*cm$^2$), or less than or equal to 0.50 mg/(hour*cm$^2$). The volatile material transfer rate of the poly(vinyl alcohol) coated microporous membrane may range between any combination of these upper and lower values, inclusive of the recited values. For example, the volatile material transfer rate of the poly(vinyl alcohol) coated microporous membrane can be at least 0.02 mg/(hour*cm$^2$), such as from 0.04 to 0.70 mg/(hour*cm$^2$), or from 0.04 to 0.60 mg/(hour*cm$^2$), or from 0.20 to 0.60 mg/(hour*cm$^2$), or from 0.30 to 0.55 mg/(hour*cm$^2$), or from 0.35 to 0.50 mg/(hour*cm$^2$), in each case inclusive of the recited values.

The density of the microporous membrane of the poly(vinyl alcohol) coated microporous membrane of the present invention may vary widely, provided that the poly(vinyl alcohol) coated microporous membrane has a targeted volatile material transfer rate, for example, of at least 0.04 mg/(hour*cm$^2$), and when the microporous membrane (i.e., the poly(vinyl alcohol) coated microporous membrane) is exposed to a temperature increase of from 25° C. to 60° C., the volatile material transfer rate thereof increases by less than or equal to 150 percent.

Further, the density of the microporous membrane, of the poly(vinyl alcohol) coated microporous membrane, may be at least 0.7 g/cm$^3$, such as at least 0.8 g/cm$^3$ (e.g., from 0.8 to 1.2 g/cm$^3$) all inclusive of the recited values. In an embodiment of the present invention, the density of the poly(vinyl alcohol) coated microporous membrane (i.e., the density of the microporous membrane prior to application of the poly(vinyl alcohol) coating) is less than 0.8 g/cm$^3$. For example, the density of the microporous membrane, of the poly(vinyl alcohol) coated microporous membrane, may be from 0.6 to less than 0.8 g/cm$^3$, or from 0.6 to 0.75 g/cm$^3$ (e.g., from 0.60 to 0.75 g/cm$^3$) or from 0.6 to 0.7 g/cm$^3$ (e.g., from 0.60 to 0.70 g/cm$^3$), or from 0.65 to 0.70 g/cm$^3$, all inclusive of the recited values.

With the poly(vinyl alcohol) coated microporous membrane of the present invention, when volatile material is transferred from the volatile material contact surface to the vapor release surface, the vapor release surface is substantially free of volatile material in liquid form.

The poly(vinyl alcohol) coating may be selected from liquid coatings which may optionally include a solvent selected from water, organic solvents and combinations thereof. The poly(vinyl alcohol) coating may be selected from crosslinkable coatings (e.g., thermosetting coatings), and non-crosslinkable coatings (e.g., air-dry coatings). The poly(vinyl alcohol) coating may be applied to the respective surfaces of the microporous membrane in accordance with art-recognized methods, such as spray application, curtain coating, or drawn-down coating (e.g., by means of a doctor blade or draw-down bar).

In an embodiment of the present invention, the first and second poly(vinyl alcohol) coatings are each independently formed from aqueous poly(vinyl alcohol) coating compositions. The solids of the aqueous poly(vinyl alcohol) coating composition may vary widely, for example from 0.1 to 15 percent by weight, or from 0.5 to 9 percent by weight, in each case based on total weight of the aqueous coating composition. The poly(vinyl alcohol) polymer of the poly(vinyl alcohol) coating compositions may have number average molecular weights (Mn) of, for example, from 100 to 1,000,000, or from 1000 to 750,000.

The poly(vinyl alcohol) polymer of the poly(vinyl alcohol) coating composition may be a homopolymer or copolymer. Co-monomer from which the poly(vinyl alcohol) copolymer may be prepared include those which are copolymerizable (by means of radical polymerization) with vinyl acetate, and which are known to the skilled artisan. For purposes of illustration, comonomers from which the poly(vinyl alcohol) copolymer may be prepared include, but are not limited to: (meth)acrylic acid, maleic acid, fumaric acid, crotonic acid, metal salts thereof, alkyl esters thereof (e.g., $C_2$-$C_{10}$ alkyl esters thereof), polyethylene glycol esters thereof, and polypropylene glycol esters thereof; vinyl chloride; tetrafluoroethylene; 2-acrylamido-2-methyl-propane sulfonic acid and its salts; acrylamide; N-alkyl acrylamide; N,N-dialkyl substituted acrylamides; and N-vinyl formamide.

For purposes of non-limiting illustration, an example of poly(vinyl alcohol) coating composition that may be used to form the poly(vinyl alcohol) coated microporous membrane of the present invention, is CELVOL 325, which is commercially available from Sekisui Specialty Chemicals.

The first and second poly(vinyl alcohol) coating compositions each independently can include art-recognized additives, such as antioxidants, ultraviolet light stabilizers, flow control agents, dispersion stabilizers (e.g., in the case of aqueous dispersions), and colorants (e.g., dyes and/or pigments). Typically, the first and second poly(vinyl alcohol)coating compositions are free of colorants, and are as such substantially clear or opaque. Optional additives may be present in the poly(vinyl alcohol) coating compositions in individual amounts of from, for example, 0.01 to 10 percent by weight, based on the total weight of the coating composition.

Matrix

The matrix of the microporous membrane is composed of substantially water-insoluble thermoplastic organic polymer. Such polymers suitable for use as the matrix can widely vary. In general, any substantially water-insoluble thermoplastic organic polymer which can be extruded, calendered, pressed, or rolled into film, sheet, strip, or web may be used. The polymer may be a single polymer or it may be a mixture of polymers. The polymers may be homopolymers, copolymers, random copolymers, block copolymers, graft copolymers, atactic polymers, isotactic polymers, syndiotactic polymers, linear polymers, or branched polymers. When mixtures of polymers are used, the mixture may be homogeneous or it may comprise two or more polymeric phases.

Examples of classes of suitable substantially water-insoluble thermoplastic organic polymers include thermoplastic polyolefins, poly(halo-substituted olefins), polyesters, polyamides, polyurethanes, polyureas, poly(vinyl halides), poly(vinylidene halides), polystyrenes, poly(vinyl esters), polycarbonates, polyethers, polysulfides, polyimides, polysilanes, polysiloxanes, polycaprolactones, polyacrylates, and polymethacrylates. Hybrid classes, from which the water-insoluble thermoplastic organic polymers may be selected include, for example, thermoplastic poly(urethane-ureas), poly(ester-amides), poly(silane-siloxanes), and poly(ether-esters) are within contemplation. Further examples of suitable substantially water-insoluble thermoplastic organic polymers include thermoplastic high density polyethylene, low density polyethylene, ultra high molecular weight polyethylene ("UHMWPE"), polypropylene (atactic, isotactic, or syndiotactic), poly(vinyl chloride), polytetrafluoroethylene, copolymers of ethylene and acrylic acid, copolymers of ethylene and methacrylic acid, poly(vinylidene chloride), copolymers of vinylidene chloride and vinyl acetate, copolymers of vinylidene chloride and vinyl chloride, copolymers of ethylene and propylene, copolymers of ethylene and butene, poly(vinyl acetate), polystyrene, poly(omega-aminoundecanoic acid) poly(hexamethylene adipamide), poly(epsilon-caprolactam), and poly(methyl methacrylate). The recitation of these classes and example of substantially water-insoluble thermoplastic organic polymers is not exhaustive, and are provided for purposes of illustration.

Substantially water-insoluble thermoplastic organic polymers may in particular include, for example, poly(vinyl chloride), copolymers of vinyl chloride, or mixtures thereof. In an embodiment the water-insoluble thermoplastic organic polymer includes an ultrahigh molecular weight polyolefin selected from: ultrahigh molecular weight polyolefin (e.g., essentially linear ultrahigh molecular weight polyolefin) having an intrinsic viscosity of at least 10 deciliters/gram; or ultrahigh molecular weight polypropylene (e.g., essentially linear ultrahigh molecular weight polypropylene) having an intrinsic viscosity of at least 6 deciliters/gram; or a mixture thereof. In a particular embodiment, the water-insoluble thermoplastic organic polymer includes UHMWPE (e.g., linear ultrahigh molecular weight polyethylene) having an intrinsic viscosity of at least 18 deciliters/gram.

UHMWPE is not a thermoset polymer having an infinite molecular weight, it is technically classified as a thermoplastic. However, because the molecules are substantially very long chains, UHMWPE softens when heated but does not flow as a molten liquid in a normal thermoplastic manner. The very long chains and the peculiar properties they provide to UHMWPE are believed to contribute in large measure to the desirable properties of microporous membranes made using this polymer.

As indicated previously, the intrinsic viscosity of the UHMWPE is at least about 10 deciliters/gram. Usually the intrinsic viscosity is at least about 14 deciliters/gram. Often the intrinsic viscosity is at least about 18 deciliters/gram. In many cases the intrinsic viscosity is at least about 19 deciliters/gram. Although there is no particular restriction on the upper limit of the intrinsic viscosity, the intrinsic viscosity is frequently in the range of from about 10 to about 39 deciliters/gram. The intrinsic viscosity is often in the range of from about 14 to about 39 deciliters/gram. In most cases the intrinsic viscosity is in the range of from about 18 to about 39 deciliters/gram. An intrinsic viscosity in the range of from about 18 to about 32 deciliters/gram is preferred.

The nominal molecular weight of UHMWPE is empirically related to the intrinsic viscosity of the polymer according to the equation:

$$M(UHMWPE) = 5.3 \times 10^4 [\eta]^{1.37}$$

where M(UHMWPE) is the nominal molecular weight and [η] is the intrinsic viscosity of the UHMW polyethylene expressed in deciliters/gram.

As used herein, intrinsic viscosity is determined by extrapolating to zero concentration the reduced viscosities or the inherent viscosities of several dilute solutions of the UHMWPE where the solvent is freshly distilled decahydronaphthalene to which 0.2 percent by weight, 3,5-di-tert-butyl-4-hydroxyhydrocinnamic acid, neopentanetetrayl ester [CAS Registry No. 6683-19-8] has been added. The reduced viscosities or the inherent viscosities of the UHMWPE are ascertained from relative viscosities obtained at 135.degree. C. using an Ubbelohde No. 1 viscometer in accordance with the general procedures of ASTM D 4020-81, except that several dilute solutions of differing concentration are employed. ASTM D 4020-81 is, in its entirety, incorporated herein by reference.

The matrix can comprise a mixture of substantially linear UHMWPE having an intrinsic viscosity of at least 10 deciliters/gram, and lower molecular weight polyethylene having an ASTM D 1238-86 Condition E melt index of less than 50 grams/10 minutes and an ASTM D 1238-86 Condition F melt index of at least 0.1 gram/10 minutes. The nominal molecular weight of the lower molecular weight polyethylene (LMWPE) is lower than that of the UHMWPE. LMWPE is thermoplastic and many different types are known. One method of classification is by density, expressed in grams/cubic centimeter and rounded to the nearest thousandth, in accordance with ASTM D 1248-84 (re-approved 1989), as summarized in the following Table 1.

TABLE 1

| Type | Abbreviation | Density (g/cm³) |
|---|---|---|
| Low Density Polyethylene | LDPE | 0.910-0.925 |
| Medium Density Polyethylene | MDPE | 0.926-0.940 |
| High Density Polyethylene | HDPE | 0.941-0.965 |

Any or all of these polyethylenes may be used as the LMWPE in the microporous membrane of the present invention. For some applications, HDPE may be used because it ordinarily tends to be more linear than MDPE or LDPE. ASTM D 1248-84 (Reapproved 1989) is, in its entirety, incorporated herein by reference.

Processes for making the various LMWPE's are well known and well documented. They include the high pressure process, the Phillips Petroleum Company process, the Standard Oil Company (Indiana) process, and the Ziegler process. The ASTM D 1238-86 Condition E (that is, 190.degree. C. and 2.16 kilogram load) melt index of the LMWPE is less than about 50 grams/10 minutes. Often the Condition E melt index is less than about 25 grams/10 minutes. Preferably the Condition E melt index is less than about 15 grams/10 minutes. The ASTM D 1238-86 Condition F (that is, 190.degree. C. and 21.6 kilogram load) melt index of the LMWPE is at least 0.1 gram/10 minutes. In many cases the Condition F melt index is at least about 0.5 gram/10 minutes. Preferably the Condition F melt index is at least about 1.0 gram/10 minutes. ASTM D 1238-86 is, in its entirety, incorporated herein by reference.

Sufficient UHMWPE and LMWPE should be present in the matrix to provide their properties to the microporous membrane. Other thermoplastic organic polymer may also be present in the matrix so long as its presence does not materially affect the properties of the microporous membrane in an adverse manner. The other thermoplastic polymer may be one other thermoplastic polymer or it may be more than one other thermoplastic polymer. The amount of the other thermoplastic polymer which may be present depends upon the nature of such polymer. Examples of thermoplastic organic polymers which may optionally be present include poly(tetrafluoroethylene), polypropylene, copolymers of ethylene and propylene, copolymers of ethylene and acrylic acid, and copolymers of ethylene and methacrylic acid. If desired, all or a portion of the carboxyl groups of carboxyl-containing copolymers may be neutralized with sodium, zinc, or the like.

The UHMWPE and the LMWPE together can constitute at least 65 percent by weight of the polymer of the matrix, such as at least 85 percent by weight of the polymer of the matrix, or the UHMWPE and the LMWPE together can constitute substantially 100 percent by weight of the polymer of the matrix. The UHMWPE can constitute at least one percent by weight of the polymer of the matrix, and the UHMWPE and the LMWPE together constitute substantially 100 percent by weight of the polymer of the matrix.

Where the UHMWPE and the LMWPE together constitute 100 percent by weight of the polymer of the matrix of the microporous membrane, the UHMWPE can constitute greater than or equal to 40 percent by weight of the polymer of the matrix, such as greater than or equal to 45 percent by weight, or greater than or equal to 48 percent by weight, or greater than or equal to 50 percent by weight, or greater than or equal to 55 percent by weight of the polymer of the matrix. Also, the UHMWPE can constitute less than or equal to 99 percent by weight of the polymer of the matrix, such as less than or equal to 80 percent by weight, or less than or equal to 70 percent by weight, or less than or equal to 65 percent by weight, or less than or equal to 60 percent by weight of the polymer of the matrix. The level of UHMWPE comprising the polymer of the matrix can range between any of these values inclusive of the recited values.

Likewise, where the UHMWPE and the LMWPE together constitute 100 percent by weight of the polymer of the matrix of the microporous membrane, the LMWPE can constitute greater than or equal to 1 percent by weight of the polymer of the matrix, such as greater than or equal to 5 percent by weight, or greater than or equal to 10 percent by weight, or greater than or equal to 15 percent by weight, or greater than or equal to 20 percent by weight, or greater than or equal to 25 percent by weight, or greater than or equal to 30 percent by weight, or greater than or equal to 35 percent by weight, or greater than or equal to 40 percent by weight, or greater than or equal to 45 percent by weight, or greater than or equal to 50 percent by weight, or greater than or equal to 55 percent by weight of the polymer of the matrix. Also, the LMWPE can constitute less than or equal to 70 percent by weight of the polymer of the matrix, such as less than or equal to 65 percent by weight, or less than or equal to 60 percent by weight, or less than or equal to 55 percent by weight, or less than or equal to 50 percent by weight, or less than or equal to 45 percent by weight of the polymer of the matrix. The level of the LMWPE can range between any of these values inclusive of the recited values.

It should be noted that for any of the previously described microporous membranes of the present invention, the LMWPE can comprise high density polyethylene.

Fillers

The microporous membrane may be filled with any suitable filler and plasticizer known in the art. Fillers may include finely-divided, substantially water-insoluble particulate filler material such as finely divided silica, clays, zeolites, carbonates, charcoals, and mixtures thereof. The particulate filler material may include an organic particulate material and/or an inorganic particulate material. The particulate filler material typically is not colored, for example, the particulate filler material is a white or off-white particulate filler material, such as a siliceous or clay particulate material.

The finely divided substantially water-insoluble filler particles may constitute from 20 to 90 percent by weight of the microporous membrane. For example, such filler particles may constitute from 20 to 90 percent by weight of the microporous membrane, such as from 30 percent to 90 percent by weight of the microporous membrane, or from 40 to 90 percent by weight of the microporous membrane, or from 40 to 85 percent by weight of the microporous membrane, or from 50 to 90 percent by weight of the microporous membrane and even from 60 percent to 90 percent by weight of the microporous membrane.

In one embodiment the microporous membrane may be filled with about 50% to about 80%, by total weight, of silica, alternatively about 60% to about 80%, alternatively about 70% to about 80%, alternatively about 70% to about 75%.

The finely divided substantially water-insoluble particulate filler may be in the form of ultimate particles, aggregates of ultimate particles, or a combination of both. At least about 90 percent by weight of the filler used in preparing the microporous membrane has gross particle sizes in the range of from 0.5 to about 200 micrometers, such as from 1 to 100 micrometers, as determined by the use of a laser diffraction particle size instrument, LS230 from Beckman Coulton, capable of measuring particle diameters as small as 0.04 micron. Typically, at least 90 percent by weight of the particulate filler has gross particle sizes in the range of from 10 to 30 micrometers. The sizes of the filler agglomerates may be reduced during processing of the ingredients used to prepare the microporous membrane. Accordingly, the distribution of gross particle sizes in the microporous membrane may be smaller than in the raw filler itself.

Non-limiting examples of suitable organic and inorganic particulate materials, that may be used in the microporous membrane of the present invention, include those described in U.S. Pat. No. 6,387,519 B1 at column 9, line 4 to column 13, line 62, the cited portions of which are incorporated herein by reference.

In a particular embodiment of the present invention, the particulate filler material comprises siliceous materials. Non-limiting examples of siliceous fillers that may be used to prepare the microporous membrane include silica, mica, montmorillonite, kaolinite, nanoclays such as cloisite available from Southern Clay Products, talc, diatomaceous earth, vermiculite, natural and synthetic zeolites, calcium silicate, aluminum silicate, sodium aluminum silicate, aluminum polysilicate, alumina silica gels and glass particles. In addition to the siliceous fillers, other finely divided particulate substantially water-insoluble fillers optionally may also be employed. Non-limiting examples of such optional particulate fillers include carbon black, charcoal, graphite, titanium oxide, iron oxide, copper oxide, zinc oxide, antimony oxide, zirconia, magnesia, alumina, molybdenum disulfide, zinc sulfide, barium sulfate, strontium sulfate, calcium carbonate, and magnesium carbonate. In a non-limiting embodiment, the siliceous filler may include silica and any of the aforementioned clays. Non-limiting examples of silicas include precipitated silica, silica gel, fumed silica, and combinations thereof.

Silica gel is generally produced commercially by acidifying an aqueous solution of a soluble metal silicate, e.g., sodium silicate at low pH with acid. The acid employed is generally a strong mineral acid such as sulfuric acid or hydrochloric acid, although carbon dioxide can be used. Inasmuch as there is essentially no difference in density between the gel phase and the surrounding liquid phase while the viscosity is low, the gel phase does not settle out, that is to say, it does not precipitate. Consequently, silica gel may be described as a non-precipitated, coherent, rigid, three-dimensional network of contiguous particles of colloidal amorphous silica. The state of subdivision ranges from large, solid masses to sub-microscopic particles, and the degree of hydration from almost anhydrous silica to soft gelatinous masses containing on the order of 100 parts of water per part of silica by weight.

Precipitated silica generally is produced commercially by combining an aqueous solution of a soluble metal silicate, ordinarily alkali metal silicate such as sodium silicate, and an acid so that colloidal particles of silica will grow in a weakly alkaline solution and be coagulated by the alkali metal ions of the resulting soluble alkali metal salt. Various acids may be used, including but not limited to mineral acids. Non-limiting examples of acids that may be used include hydrochloric acid and sulfuric acid, but carbon dioxide can also be used to produce precipitated silica. In the absence of a coagulant, silica is not precipitated from solution at any pH. In a non-limiting embodiment, the coagulant used to effect precipitation of silica may be the soluble alkali metal salt produced during formation of the colloidal silica particles, or it may be an added electrolyte, such as a soluble inorganic or organic salt, or it may be a combination of both.

Precipitated silicas are available in many grades and forms from PPG Industries, Inc. These silicas are sold under the Hi-Sil® tradename.

For purposes of the present invention, the finely divided particulate substantially water-insoluble siliceous filler can comprise at least 50 percent by weight (e.g., at least 65, at least 75 percent by weight), or at least 90 percent by weight of the substantially water-insoluble filler material. The siliceous filler may comprise from 50 to 90 percent by weight (e.g., from 60 to 80 percent by weight) of the particulate filler material, or the siliceous filler may comprise substantially all of the substantially water-insoluble particulate filler material.

The particulate filler (e.g., the siliceous filler) typically has a high surface area allowing the filler to carry much of the processing plasticizer composition used to produce the microporous membrane of the present invention. The filler particles are substantially water-insoluble and also can be substantially insoluble in any organic processing liquid used to prepare the microporous membrane. This can facilitate retention of the particulate filler within the microporous membrane.

The microporous membrane of the present may also include minor amounts (e.g., less than or equal to 5 percent by weight, based on total weight of the microporous membrane) of other materials used in processing, such as lubricant, processing plasticizer, organic extraction liquid, water, and the like. Further materials introduced for particular purposes, such as thermal, ultraviolet and dimensional stability, may optionally be present in the microporous membrane in small amounts (e.g., less than or equal to 15 percent by weight, based on total weight of the microporous membrane).

Examples of such further materials include, but are not limited to, antioxidants, ultraviolet light absorbers, reinforcing fibers such as chopped glass fiber strand, and the like. The balance of the microporous membrane, exclusive of filler and any coating, printing ink, or impregnant applied for one or more special purposes is essentially the thermoplastic organic polymer.

Pores

The microporous membrane of the present invention, also includes a network of interconnecting pores, which communicate substantially throughout the microporous membrane. On a coating-free, printing ink free and impregnant-free basis, pores typically constitute from 35 to 95 percent by volume, based on the total volume of the microporous membrane, when made by the processes as further described herein. The pores may constitute from 60 to 75 percent by volume of the microporous membrane, based on the total volume of the microporous membrane.

As used herein and in the claims, the porosity (also known as void volume) of the microporous membrane, expressed as percent by volume, is determined according to the following equation:

$$\text{Porosity} = 100[1 - d_1/d_2]$$

where, $d_1$ is the density of the sample, which is determined from the sample weight and the sample volume as ascertained from measurements of the sample dimensions; and $d_2$ is the density of the solid portion of the sample, which is determined from the sample weight and the volume of the solid portion of the sample. The volume of the solid portion of the microporous membrane is determined using a Quantachrome stereopycnometer (Quantachrome Corp.) in accordance with the operating manual accompanying the instrument.

The volume average diameter of the pores of the microporous membrane is determined by mercury porosimetry using an Autoscan mercury porosimeter (Quantachrome Corp.) in accordance with the operating manual accompanying the instrument. The volume average pore radius for a single scan is automatically determined by the porosimeter. In operating the porosimeter, a scan is made in the high pressure range (from 138 kilopascals absolute to 227 megapascals absolute). If 2 percent or less of the total intruded volume occurs at the low end (from 138 to 250 kilopascals absolute) of the high pressure range, the volume average pore diameter is taken as twice the volume average pore radius determined by the porosimeter. Otherwise, an additional scan is made in the low pressure range (from 7 to 165 kilopascals absolute) and the volume average pore diameter is calculated according to the equation:

$$d = 2[v_1 r_1/w_1 + v_2 r_2/w_2]/[v_1/w_1 + v_2/w_2]$$

where, d is the volume average pore diameter; $v_1$ is the total volume of mercury intruded in the high pressure range; $v_2$ is the total volume of mercury intruded in the low pressure range; $r_1$ is the volume average pore radius determined from the high pressure scan; $r_2$ is the volume average pore radius determined from the low pressure scan; $w_1$ is the weight of the sample subjected to the high pressure scan; and $w_2$ is the weight of the sample subjected to the low pressure scan.

The microporous membrane of the present invention may have an average pore size of about 0.01 to about 0.06 microns, alternatively from about 0.01 to about 0.05 microns, alternatively about 0.01 to about 0.04, alternatively about 0.01 to about 0.03, alternatively about 0.02 to about 0.04 microns, alternatively about 0.02 microns.

Generally on a coating-free, printing ink-free and impregnant-free basis, the volume average diameter of the pores of the microporous membrane is at least 0.02 micrometers, typically at least 0.04 micrometers, and more typically at least 0.05 micrometers. On the same basis, the volume average diameter of the pores of the microporous membrane is also typically less than or equal to 0.5 micrometers, more typically less than or equal to 0.3 micrometers, and further typically less than or equal to 0.25 micrometers. The volume average diameter of the pores, on this basis, may range between any of these values, inclusive of the recited values. For example, the volume average diameter of the pores of the microporous membrane may range from 0.02 to 0.5 micrometers, or from 0.04 to 0.3 micrometers, or from 0.05 to 0.25 micrometers, in each case inclusive of the recited values.

In the course of determining the volume average pore diameter by means of the above described procedure, the maximum pore radius detected may also be determined. This is taken from the low pressure range scan, if run; otherwise it is taken from the high pressure range scan. The maximum pore diameter of the microporous membrane is typically twice the maximum pore radius.

Coating, printing and impregnation processes can result in filling at least some of the pores of the microporous membrane. In addition, such processes may also irreversibly compress the microporous membrane. Accordingly, the parameters with respect to porosity, volume average diameter of the pores, and maximum pore diameter are determined for the microporous membrane prior to application of one or more of these processes.

Thickness and Surface Area

The microporous membrane may have a thickness in the z-direction, of about 0.01 mm to about 1 mm, alternatively between about 0.1 mm to 0.4 mm, alternatively about 0.15 mm to about 0.35 mm, alternatively about 0.25 mm.

Those of ordinary skill in the art will appreciate that the surface area of the microporous membrane can vary depending on the user preferred size of the delivery engine 100. In some embodiments, the evaporative surface area of the microporous membrane may be about 2 cm$^2$ to about 100 cm$^2$, alternatively about 2 cm$^2$ to about 35 cm$^2$, alternatively about 10 cm$^2$ to about 50 cm$^2$, alternatively about 10 cm$^2$ to about 45 cm$^2$, alternatively about 10 cm$^2$ to about 35 cm$^2$, alternatively about 15 cm$^2$ to about 40 cm$^2$, alternatively about 15 cm$^2$ to about 35 cm$^2$, alternatively about 20 cm$^2$ to about 35 cm$^2$, alternatively about 30 cm$^2$ to about 35 cm$^2$, alternatively about 35 cm$^2$.

Suitable microporous membranes for the present invention include an UHMWPE-type membrane optionally filled with silica as described in U.S. Pat. No. 7,498,369. Such UHMWPE membranes include Daramic™ V5, available from Daramic, Solupor®, available from DSM (Netherlands), and Teslin™ SP1100HD, available from PPG Industries, and combinations thereof. It is believed that these membranes allow a volatile material to freely dissipate, while containing liquid within the delivery engine 100.

In one aspect of the invention, the microporous membrane may include a dye that is sensitive to the amount of volatile material it is in contact with to indicate end-of-life. Alternatively, the microporous membrane may change to transparent when in contact with a fragrance or volatile material to indicate diffusion is occurring. Other means for indicating end-of-life that are known in the art are contemplated for the present invention.

Housing

Now referring to FIGS. 6 to 9, the apparatus 10 of the present invention may include a housing 200 for releasably engaging the delivery engine 100. The housing 200 may comprise a width, length and depth along an x-axis, y-axis, and z-axis, respectively (as shown in FIG. 1). The housing 200 can be made of any suitable material such as glass, ceramic, wood, plastic, composite material, etc, and can have any size, shape and configuration suitable for encasing the delivery engine 100. The housing 200 can be rigid or flexible and can be made of material which allows the transfer of volatile materials to the surrounding environment. The housing 200 may include a base 210, a hollowed core 240 supported on the base 210 and nested internally within a shell 220. The housing 200 may also include a notch 270 and vents 260.

Shell and Hollowed Core

Figure 8:
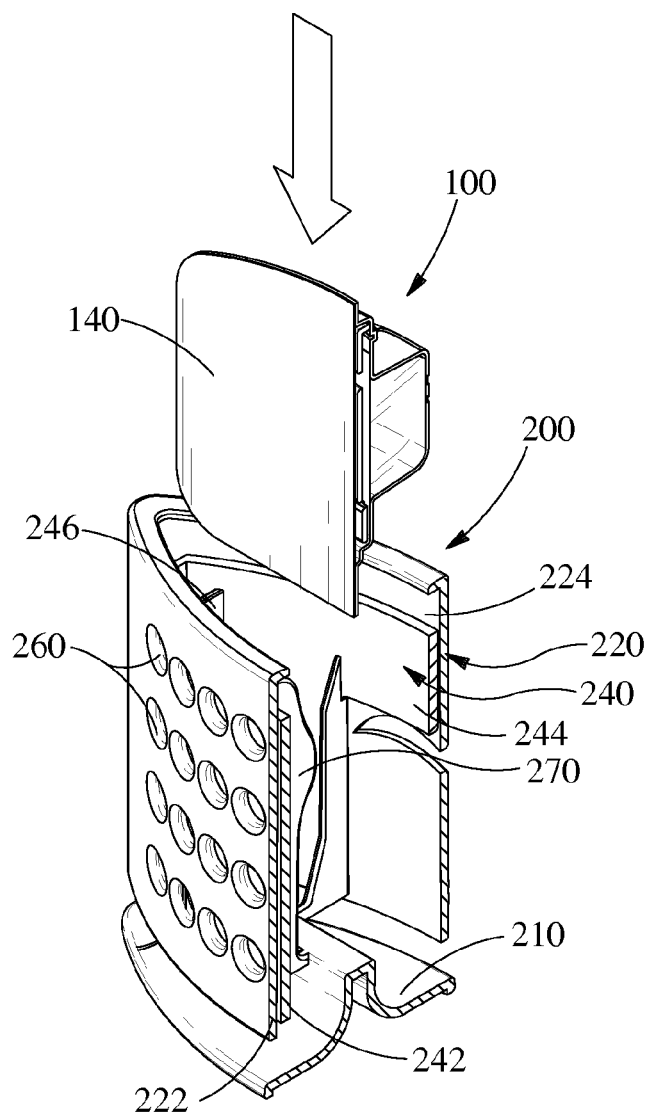
FIG. 8 shows a cross-sectional view along lines 8-8 of the apparatus in FIG. 1.
Figure 9:
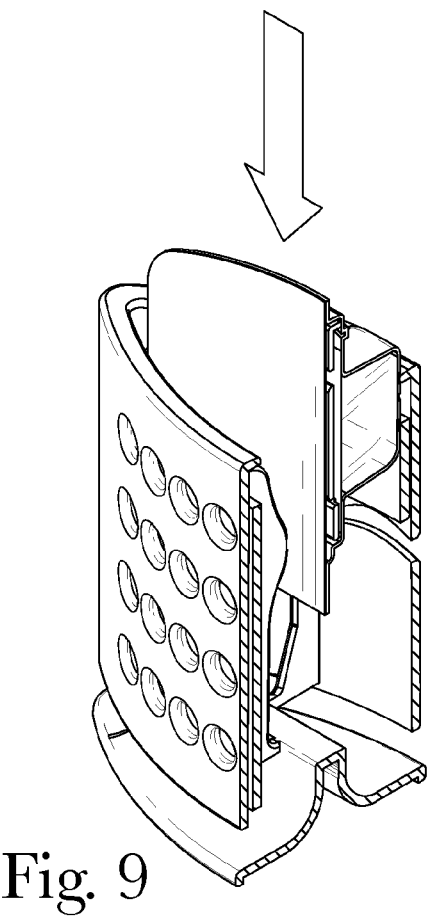
FIG. 9 shows the cross-sectional view in FIG. 8 where the delivery engine is being received by the housing.

As seen in FIGS. 8 and 9, the housing 100 may include a hollowed core 240 supported on a base 210 and nested internally within a shell 220. The shell 220 may have a front wall 222 and a rear wall 224, both of which may be generally coextensive with a front wall 242 and a rear wall 244 of the hollowed core 240. The hollowed core 240 and shell 220 may be elliptically cylindrical and include a receiving end 230 for receiving the delivery engine 100. The receiving end 230 may be disposed remotely from the base 210 of the housing 200.

Ribs and Notches

The inner face of the rear wall 244 of the hollowed core 240 may include one or more retaining ribs 246 for guiding the delivery engine 100 downward into its final in-use position as seen in FIG. 9. In one embodiment, the retaining ribs 246 may include a first retaining rib and a second retaining rib positioned on the inner face of the rear wall 244 and which both extend longitudinally along the y-axis. The first and second retaining ribs may be positioned at the intersection of the front 242 and rear walls 244 of the hollowed core 240 to receive the lip 102 of the delivery engine 100.

The housing 200 may also include a notch 270, or a plurality of notches, to engage or compress the rupture element 130 as the delivery engine 100 is being received in the housing 200. In this way, a user is not required to manually activate the delivery engine 100 prior to its insertion into the housing 200. The notch 270 may be configured in any manner such that the delivery engine 100 can be inserted into the housing 200 with relative ease while the notch 270 compresses the rupture element 130 and breaches the rupturable substrate 120.

Suitable insertion forces to insert the delivery engine 100 which compresses the rupture element 130 and breaches the rupturable substrate 120 include less than about 25N, alternatively less than about 20N, alternatively less than about 15N, alternatively less than about 5N, alternatively from about 1N to about 25N, alternatively from about 1N to about 15N, alternatively from about 5N to about 20N, alternatively from about 5N to about 15N, alternatively about 8 to 15 N.

The insertion force can be measured using an electromechanical testing system, QTest Elite 10 available from MTS. The delivery engine 100 is clamped to the testing system and placed in the receiving end of the housing without any force against any notch 270 or elements that breach or help breach the rupturable substrate 120. The crosshead speed of the electromechanical testing system is set at 50 mm/min. The room temperature is 23+2° C. The machine is run until the rupturable substrate 120 is breached. Zero displacement is defined as the point at which 0.1N of force (i.e. preload) is applied. The load at the first peak where the rupture substrate 120 is broken is recorded as the force to rupture. Those of ordinary skill in the art will appreciate that insertion forces will vary depending on the physical properties and placement of the notch 270, breathable membrane 140, rupture element 130, and rupturable substrate 120.

In one embodiment, the notch 270 may be laterally off-set from the center of the front wall 242 of the hollowed core 240, so that less projection of the notch 270 in the z-direction is required when manufacturing. Thus, the breathable membrane 140 does not need to be stretched as far, resulting in less likelihood of damage.

The notch 270 and ribs 246 are configured such that the delivery engine 100 does not need to bend when inserting, resulting in lower insertion force. As the delivery engine 100 is inserted into the housing 200, the notch 270 compresses the breathable membrane 140 and the rupture element 130 in the direction of the reservoir 110 to breach the rupturable substrate 120 and release volatile materials to the breathable membrane 140. During insertion of the delivery engine 100, the ribs 246 guide the delivery engine 100 into contact and against the notch 270, maintaining the lateral position of the delivery engine 100 so the notch 270 fully engages the rupture element 130.

Vents

The housing 200 may have a plurality of vents 260 or apertures which align in a first, open position to facilitate delivery of the volatile material from the breathable membrane 140 to the atmosphere of the room or rooms that require treatment. Increasing the effective size of the vents 260, may increase the delivery of volatile material. Conversely, decreasing the effective size of the vents 260, may decrease the delivery of volatile material.

The vents 260 may be disposed anywhere on the housing 200. In the embodiment shown in FIGS. 6 to 9, the vents 260 are disposed on the front walls 222, 242 of shell 220 and hollowed core 240. The number and/or size of the vents 260 are not fixed. The size of the vents 260 can be controlled by the user through a variety of means. A user may open, partially open, partially close, or close the one or more vents 260 by sliding the shell 220 downwardly along the y-axis towards the base 210 such that the desired amount of emission is delivered to the location needing treatment. The housing 200 may also be constructed to enable open and closing of the vents 260 by rotation of the shell 240 around the x-axis (not shown). In addition to the vents 260, the housing 200 may have other means for visual inspection of the delivery engine 100.

The housing 200 may also include a clicking mechanism (not shown) to signal to the user that the housing 200 is in the desired open or closed position. Such clicking mechanism may include a first mating part (not shown) disposed along the outer face of the hollowed core 240 and a second mating part (not shown) disposed along the inner face of the shell 220. The mating parts may frictionally engage the walls of the shell 220 and hollowed core 240 as they slide against one another. When the desired open or closed position is reached the mating parts may releasably lock into place and may provide a clicking sound.

Volatile Material

The apparatus 10 and/or the delivery engine 100 of the present invention deliver a volatile material to the atmosphere in a continuous manner. The term "volatile material" as used herein, refers to a material that is vaporizable at room temperature and atmospheric pressure without the need of an energy source. The volatile material may be a composition comprised entirely of a single volatile material. The volatile material may also be a composition comprised entirely of a volatile material mixture (i.e. the mixture has more than one volatile component). Further, it is not necessary for all of the component materials of the composition to be volatile. Any suitable volatile material in any amount or form, including a liquid or emulsion, may be used.

Liquid suitable for use herein may, thus, also have non-volatile components, such as carrier materials (e.g., water, solvents, etc). It should also be understood that when the liquid is described herein as being "delivered", "emitted", or "released," this refers to the volatilization of the volatile component thereof, and does not require that the non-volatile components thereof be emitted.

The volatile material can be in the form of perfume oil. Most conventional fragrance materials are volatile essential oils. The volatile material can be a volatile organic compound commonly available from perfumery suppliers. Furthermore, the volatile material can be synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like. In the case of air freshener or fragrances, the different volatile materials can be similar, related, complementary, or contrasting.

The volatile material may also originate in the form of a crystalline solid, which has the ability to sublime into the vapor phase at ambient temperatures or be used to fragrance a liquid. Any suitable crystalline solid in any suitable amount or form may be used. For example, suitable crystalline solids include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evemyl, and the like.

It may not be desirable, however, for volatile materials to be closely similar if different volatile materials are being used in an attempt to avoid the problem of emission habituation. Otherwise, the people experiencing the emissions may not notice that a different material is being emitted. The different emissions can be provided using a plurality of delivery systems each providing a different volatile material (such as, musk, floral, fruit emissions, etc). The different emissions can be related to each other by a common theme, or in some other manner. An example of emissions that are different, but complementary might be a cinnamon emission and an apple emission.

In addition to the volatile material of the present invention, the delivery engine 100 may include any known malodor composition to neutralize odors. Suitable malodor compositions include cyclodextrin, reactive aldehydes and ionones.

While not wishing to be bound by theory, the continuous delivery of a volatile material may be a function of various factors including membrane pore size; membrane surface area; the physical properties of a volatile material, such as molecular weight and saturation vapor pressure ("VP"); and the viscosity and/or surface tension of the composition containing the volatile material.

The composition may be formulated such that the composition comprises a volatile material mixture comprising about 10% to about 100%, by total weight, of volatile materials that each having a VP at 25° C. of less than about 0.01 torr; alternatively about 40% to about 100%, by total weight, of volatile materials each having a VP at 25° C. of less than about 0.1 torr; alternatively about 50% to about 100%, by total weight, of volatile materials each having a VP at 25° C. of less than about 0.1 torr; alternatively about 90% to about 100%, by total weight, of volatile materials each having a VP at 25° C. of less than about 0.3 torr. In one embodiment, the volatile material mixture may include 0% to about 15%, by total weight, of volatile materials each having a VP at 25° C. of about 0.004 torr to about 0.035 torr; and 0% to about 25%, by total weight, of volatile materials each having a VP at 25° C.

of about 0.1 torr to about 0.325 torr; and about 65% to about 100%, by total weight, of volatile materials each having a VP at 25° C. of about 0.035 ton to about 0.1 torr. One source for obtaining the saturation vapor pressure of a volatile material is EPI Suite™, version 4.0, available from U.S. Environmental Protection Agency.

Two exemplary compositions comprising a volatile material mixture having volatile materials of varying VPs are set forth below in Tables 2 and 3. These compositions are shown by way of illustration and are not intended to be in any way limiting of the invention.

TABLE 2

| Wt % | Low VP (torr) | High VP (torr) |
|---|---|---|
| 27.71 | 0.14 | 0.325 |
| 20.78 | 0.0875 | 0.14 |
| 13.86 | 0.0625 | 0.0875 |
| 8.66 | 0.035 | 0.0625 |
| 8.66 | 0.014 | 0.035 |
| 6.93 | 0.00875 | 0.014 |
| 6.93 | 0.00625 | 0.00875 |
| 3.18 | 0.0035 | 0.00625 |
| 1.27 | 0.0014 | 0.0035 |
| 0.95 | 0.000875 | 0.0014 |
| 0.64 | 0.000625 | 0.000875 |
| 0.32 | 0.000375 | 0.000625 |
| 0.09 | 0.000175 | 0.000325 |

TABLE 3

| Wt % | Low VP (torr) | High VP (torr) |
|---|---|---|
| 33.38 | 0.14 | 0.325 |
| 25.75 | 0.0875 | 0.14 |
| 19.07 | 0.0625 | 0.0875 |
| 13.86 | 0.035 | 0.0625 |
| 4.00 | 0.014 | 0.035 |
| 1.50 | 0.00875 | 0.014 |
| 0.50 | 0.00625 | 0.00875 |
| 0.72 | 0.0035 | 0.00625 |
| 0.55 | 0.0014 | 0.0035 |
| 0.27 | 0.000875 | 0.0014 |
| 0.20 | 0.000625 | 0.000875 |
| 0.13 | 0.000375 | 0.000625 |
| 0.07 | 0.000175 | 0.000325 |

The viscosity of a volatile material may control how and when a volatile material is delivered to the breathable membrane 140. For example, less viscous compositions may flow faster than the more viscous volatile materials. Thus, the membrane may be first wetted with the less viscous materials. The more viscous volatile material, being slightly less or of similar density with the less viscous phase, may remain in the collection basin 112 via gravity. Thus, the less viscous volatile material may be delivered to the breathable membrane 140 and emitted to the atmosphere more quickly. To help prevent liquid from seeping through the breathable membrane 140, volatile materials may have viscosities less than about 23 cP and surface tension less than about 33 mN/m.

In one embodiment, the composition containing a volatile material may have a viscosity of about 1.0 cP to less than about 25 cP, alternatively about 1.0 cP to less than about 23, alternatively about 1.0 cP to less than about 15 cP.

The composition containing a volatile material may be designed such that the composition may include a surface tension of about 19 mN/m to less than about 33 mN/m, alternatively about 19 mN/m to less than about 30 mN/m, alternatively about 19 mN/m to less than about 27 mN/m.

EXAMPLES

The following examples are not to be construed as limitations of the present invention since many variations thereof are possible without departing from its spirit and scope.

Example 1

In this example, two identical air freshening delivery engines are designed utilizing a Daramic V5 membrane with an evaporative surface area of approximately 34 cm². Two perfume compositions, RJJ-577 and RJJ-573-8, each having a volatile material mixture with volatile materials of different VP ranges are tested in the air freshening delivery engines for evaporation rates. The VP ranges of the volatile materials are shown in Tables 4 and 5.

TABLE 4

| RJJ-577 | | |
|---|---|---|
| VP 25° C. Low | VP 25° C. High | Wt % |
| 0 | 0.001 | 0.2 |
| 0.001 | 0.01 | 0.0 |
| 0.01 | 0.1 | 3.4 |
| 0.1 | 0.3 | 28.6 |
| 0.3 | 10 | 64.8 |

TABLE 5

| RJJ-573-8 | | |
|---|---|---|
| VP 25° C. Low | VP 25° C. High | Wt % |
| 0 | 0.001 | 1.9 |
| 0.001 | 0.01 | 8.5 |
| 0.01 | 0.1 | 32.6 |
| 0.1 | 0.3 | 49.8 |
| 0.3 | 10 | 6.8 |

Figure 10:
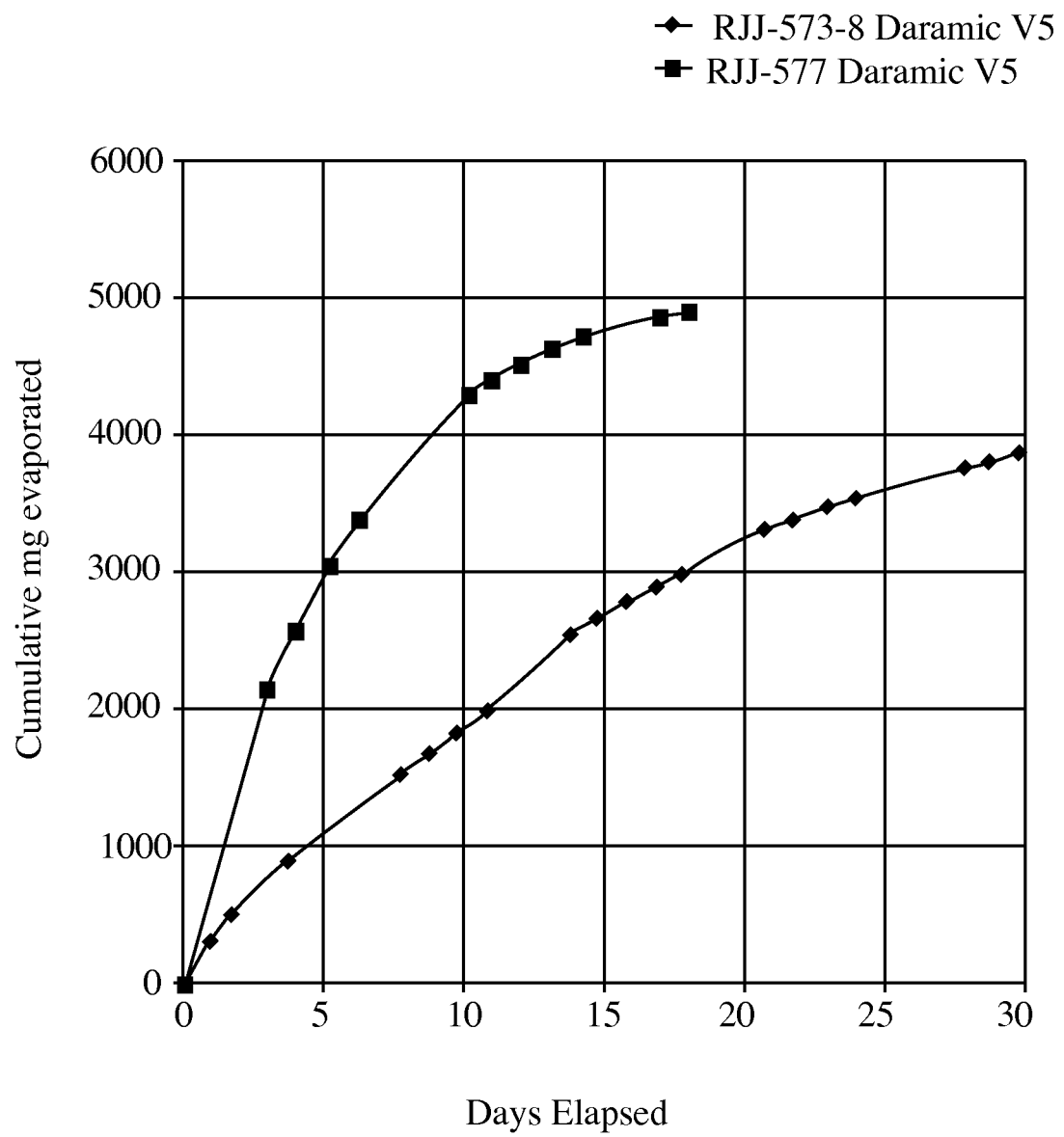
FIG. 10 is a graph showing evaporation profiles of volatile materials having varying vapor pressure ranges evaporated from a breathable membrane in accordance with the present invention

One delivery engine is loaded with 6000 mg of perfume composition RJJ-577; the other with 6000 mg of perfume composition RJJ-573-8. RJJ-577 includes relatively higher VP components than RJJ-573-8. Each filled delivery engine is weighed; weight is recorded. Both delivery engines are placed into housings and held in a room at 21° C. At the times indicated on FIG. 10, the delivery engine is weighed; weight recorded. FIG. 10 shows that after about two weeks, the evaporation rate of RJJ-577 has almost flattened which would then require another delivery engine. This would be costly and may be viewed as burdensome by consumers. On the other hand, perfume RJJ-573-8 with a microporous membrane delivers consistent linear intensity over a longer period of time.

Example 2

Figure 11:
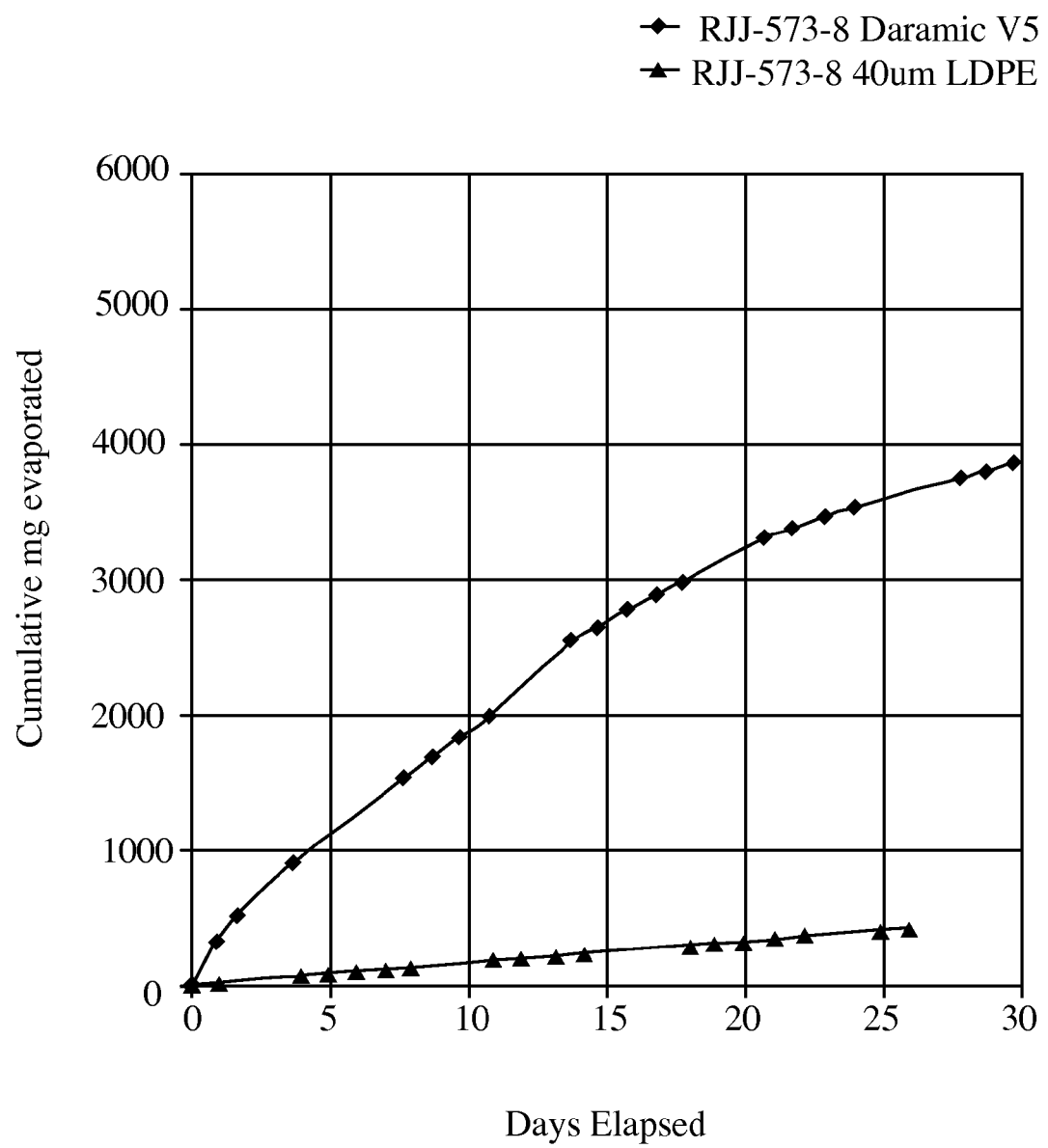
FIG. 11 is a graph showing evaporation profiles of volatile materials evaporated from a polyethylene membrane and from a breathable membrane in accordance with the present invention.

In this example, two air freshening delivery engines are constructed utilizing different membranes. Each is tested for evaporation rates using RJJ-573-8, which was utilized in Example 1. 6000 mg of RJJ-573-8 is loaded into a delivery engine with a low density polyethylene membrane (LDPE) having an average pore size of about 40 microns. 6000 mg of RJJ-573-8 is loaded into a delivery engine having a Daramic V5 microporous membrane. As can be seen from FIG. 11, the microporous membrane is much more efficient in releasing the relatively low vapor pressure perfume than the LDPE membrane. Thus, utilizing a microporous membrane in accordance with the present invention delivers higher intensities of lower vapor pressure (i.e. more pleasing "base note" perfume raw materials can be delivered).

As used in this specification and the appended claims, the singular forms "a", "an", and "the" include plural references unless the content clearly dictates otherwise. Thus, for example, "a volatile material" may include more than one volatile material Every numerical range given throughout this specification will include every narrower numerical range that falls within such broader numerical range, as if such narrower numerical range were all expressly written herein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

Further, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. An apparatus for delivering a volatile material comprising a delivery engine comprising:
    a. a reservoir comprising a volatile material mixture, said mixture comprising about 40% to about 100%, by total weight of said mixture, of volatile materials each having a VP at 25° C. of less than about 0.3 torr;
    b. a rupturable substrate secured to said reservoir;
    c. a rupture element integrally formed with said reservoir, extending opposite a z-direction, and positioned adjacent to said rupturable substrate;
    d. a microporous membrane enclosing said reservoir, said rupturable substrate and said rupture element, wherein said microporous membrane comprises an average pore size of about 0.01 microns to about 0.06 microns and an evaporative surface area of about 2 $cm^2$ to about 35 $cm^2$;
    and wherein said apparatus further comprises a housing comprising a notch extending towards said z-direction for compressing said rupture element upon insertion of said delivery engine into said housing, wherein said delivery engine provides 30 to 90 days of continuous emission of said volatile material without leakage.

2. The apparatus of claim 1, wherein said delivery engine further comprises a collection basin in fluid communication with said microporous membrane and said reservoir upon rupturing said rupturable substrate.

3. The apparatus of claim 1, wherein said rupture element is positioned between said rupturable substrate and said microporous membrane.

4. The apparatus of claim 1, wherein said rupture element is positioned subjacent said microporous membrane.

5. The apparatus of claim 1, wherein said rupture element comprises a compressible flange.

6. The apparatus of claim 5, wherein said compressible flange comprises a distal end and a piercing element, said piercing element positioned on said distal end.

7. The apparatus of claim 1, wherein the compression force of said rupture element to breach said rupturable substrate is less than about 15N.

8. The apparatus of claim 1, wherein said microporous membrane comprises an average pore size of about 0.01 to about 0.03 microns.

9. The apparatus of claim 1, wherein said microporous membrane comprises an average pore size of about 0.02 microns.

10. The apparatus of claim 1, wherein said a housing further comprises a base, a shell, and a hollowed core.

11. The apparatus of claim 10, wherein said notch is positioned in said hollowed core.

12. The apparatus of claim 11 wherein said hollowed core comprises a front wall comprising vents, wherein said notch is positioned on the inner face of said front wall.

13. The apparatus of claim 1 wherein said hollowed core comprises a first rib and a second rib for guiding said delivery engine against said notch.

14. The apparatus of claim 10, wherein said housing comprises intensity control means.

* * * * *